(12) United States Patent
Fujii

(10) Patent No.: US 12,212,880 B2
(45) Date of Patent: Jan. 28, 2025

(54) IMAGE PROCESSING APPARATUS, OBSERVATION SYSTEM, AND OBSERVATION METHOD

(71) Applicant: OLYMPUS CORPORATION, Hachioji (JP)

(72) Inventor: Toshiyuki Fujii, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 139 days.

(21) Appl. No.: 17/875,020

(22) Filed: Jul. 27, 2022

(65) Prior Publication Data
US 2022/0360723 A1 Nov. 10, 2022

Related U.S. Application Data

(63) Continuation of application No. PCT/JP2020/003283, filed on Jan. 29, 2020.

(51) Int. Cl.
*H04N 5/265* (2006.01)
*A61B 1/00* (2006.01)
(Continued)

(52) U.S. Cl.
CPC ....... *H04N 5/265* (2013.01); *A61B 1/000095* (2022.02); *A61B 1/0655* (2022.02);
(Continued)

(58) Field of Classification Search
CPC ........ H04N 5/265; H04N 7/181; H04N 23/56; H04N 23/71; H04N 23/74; H04N 23/90;
(Continued)

(56) References Cited

U.S. PATENT DOCUMENTS

| 2009/0284602 A1* | 11/2009 | Chu | H04N 23/698 |
| | | | 348/790 |
| 2010/0249700 A1* | 9/2010 | Spivey | A61B 17/29 |
| | | | 604/264 |

(Continued)

FOREIGN PATENT DOCUMENTS

| JP | S58-114011 A | 7/1983 |
| JP | 2017-142245 A | 8/2017 |

(Continued)

OTHER PUBLICATIONS

Kanhere, A et al., "Multicamera Laparoscopic Imaging with Tunable Focusing Capability", Journal of Mircoelectromechanical Systems, 2014, vol. 23, No. 6, pp. 1290-1299, cited in ISR dated Mar. 24, 2020. (10 pages).

(Continued)

*Primary Examiner* — Albert H Cutler
(74) *Attorney, Agent, or Firm* — WHDA, LLP

(57) ABSTRACT

An image processing apparatus includes a processor including hardware, the processor being configured to: determine whether or not an overlapping portion is present in imaging areas included in a plurality of images captured by a plurality of imagers, respectively, the plurality of imagers being are inserted into a subject to capture images of an observation target at different positions from each other; determine whether or not each of the plurality of imagers is inserted to a focal point position at which the observation target is in focus; and generate a composite image that is composed of the plurality of images when it is determined that each of the plurality of imagers is inserted to the focal point position and that the overlapping portion is present in the imaging areas.

17 Claims, 18 Drawing Sheets

(51) Int. Cl.
  *A61B 1/045*    (2006.01)
  *A61B 1/06*     (2006.01)
  *A61B 1/313*    (2006.01)
  *A61B 90/00*    (2016.01)
  *H04N 7/18*     (2006.01)
  *H04N 23/50*    (2023.01)
  *H04N 23/56*    (2023.01)
  *H04N 23/71*    (2023.01)
  *H04N 23/74*    (2023.01)
  *H04N 23/90*    (2023.01)

(52) U.S. Cl.
  CPC ............. *H04N 7/181* (2013.01); *H04N 23/56* (2023.01); *H04N 23/71* (2023.01); *H04N 23/74* (2023.01); *H04N 23/90* (2023.01); *A61B 1/000096* (2022.02); *A61B 1/045* (2013.01); *A61B 1/313* (2013.01); *A61B 2090/371* (2016.02); *H04N 23/555* (2023.01)

(58) Field of Classification Search
  CPC .... H04N 23/555; H04N 23/60; H04N 23/673; H04N 23/61; H04N 23/611; H04N 23/631; H04N 23/66; H04N 23/67; H04N 23/675; H04N 23/698; H04N 23/70; A61B 1/000095; A61B 1/0655; A61B 1/000096; A61B 1/045; A61B 1/313; A61B 2090/371; A61B 1/00006; A61B 1/00016; A61B 1/0005; A61B 1/00055; A61B 1/043; A61B 1/046; A61B 1/0684; A61B 1/3132; A61B 90/361; A61B 90/37; A61B 2090/3614

USPC ........................................ 348/62, 68, 72, 77
  See application file for complete search history.

(56) References Cited

U.S. PATENT DOCUMENTS

| | | | |
|---|---|---|---|
| 2014/0012139 A1 | 1/2014 | Sharonov | |
| 2017/0228884 A1 | 8/2017 | Yoshida | |
| 2018/0180407 A1* | 6/2018 | Inukai | ........................ G06T 7/50 |
| 2019/0008367 A1* | 1/2019 | Ishikawa | .............. A61B 90/361 |
| 2019/0370986 A1* | 12/2019 | Kawai | ........................ G06T 7/97 |
| 2021/0345856 A1* | 11/2021 | Uyama | .............. G02B 21/0012 |

FOREIGN PATENT DOCUMENTS

| | | |
|---|---|---|
| JP | 6599839 B2 | 10/2019 |
| WO | 2017/163407 A1 | 9/2017 |

OTHER PUBLICATIONS

International Search Report dated Mar. 24, 2020, issued in counterpart International application No. PCT/JP2020/003283. (3 pages).

* cited by examiner

IMAGE PROCESSING APPARATUS, OBSERVATION SYSTEM, AND OBSERVATION METHOD

CROSS-REFERENCE TO RELATED APPLICATION

This application is a continuation of International Application No. PCT/JP2020/003283, filed on Jan. 29, 2020, the entire contents of which are incorporated herein by reference.

BACKGROUND

1. Technical Field

The present disclosure relates to an image processing apparatus, an observation system, and an observation method.

2. Related Art

In the medical field, an observation system using an endoscope is known as a method for observing an inside of a subject in a less invasiveness manner, (for example, see Japanese Patent No. 6599839). The endoscope is provided with an imager at a distal end of an insertion portion that is inserted into the subject and outputs in-vivo images captured by the imager. The in-vivo images that are output by the endoscope are subjected to image processing by an image processing apparatus and are displayed on a display device.

SUMMARY

In some embodiments, an image processing apparatus includes a processor including hardware, the processor being configured to: determine whether or not an overlapping portion is present in imaging areas included in a plurality of images captured by a plurality of imagers, respectively, the plurality of imagers being are inserted into a subject to capture images of an observation target at different positions from each other; determine whether or not each of the plurality of imagers is inserted to a focal point position at which the observation target is in focus; and generate a composite image that is composed of the plurality of images when it is determined that each of the plurality of imagers is inserted to the focal point position and that the overlapping portion is present in the imaging areas.

In some embodiments, an observation system includes: the image processing apparatus; and the plurality of imagers configured to capture the plurality of images.

In some embodiments, an observation method includes: ensuring an observation purpose space for observing an observation target located inside a subject; inserting, into the subject, a plurality of imagers configured to capture images of the observation target at different positions from each other; guiding the plurality of imagers to a focal point position at which the observation target is in focus; determining whether or not an overlapping portion is present in imaging areas included in a plurality of images captured by the plurality of imagers, respectively; and generating, when it is determined that the overlapping portion is present at the determining, a composite image that is composed of the plurality of images.

In some embodiments, an image processing apparatus includes a processor including hardware, the processor being configured to: determine whether or not an overlapping portion is present in imaging areas included in a plurality of images captured by a plurality of imagers, respectively, the plurality of imagers being configured to capture images of an observation target at different positions from each other, the observation target being located inside a subject and that is irradiated with illumination light; and that generate, when it is determined that the overlapping portion is present in the imaging areas, a composite image that is composed of the plurality of images in which unevenness of brightness of the overlapping portion is reduced.

In some embodiments, an observation system includes: a processor comprising hardware, the processor being configured to determine whether or not an overlapping portion is present in imaging areas included in a plurality of images captured by a plurality of imagers, respectively, the plurality of imagers being are inserted into a subject to capture images of an observation target at different positions from each other, and generate a composite image that is composed of the plurality of images when it is determined that the overlapping portion is present in the imaging areas; and an illuminator that includes a guide light irradiator configured to irradiate the observation target with guide light. The processor is configured to determine whether or not the overlapping portion is present in the imaging areas by comparing the guide light on the plurality of images captured by the plurality of respective imagers, and generate the composite image by comparing the guide light on the plurality of images captured by the plurality of respective imagers.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
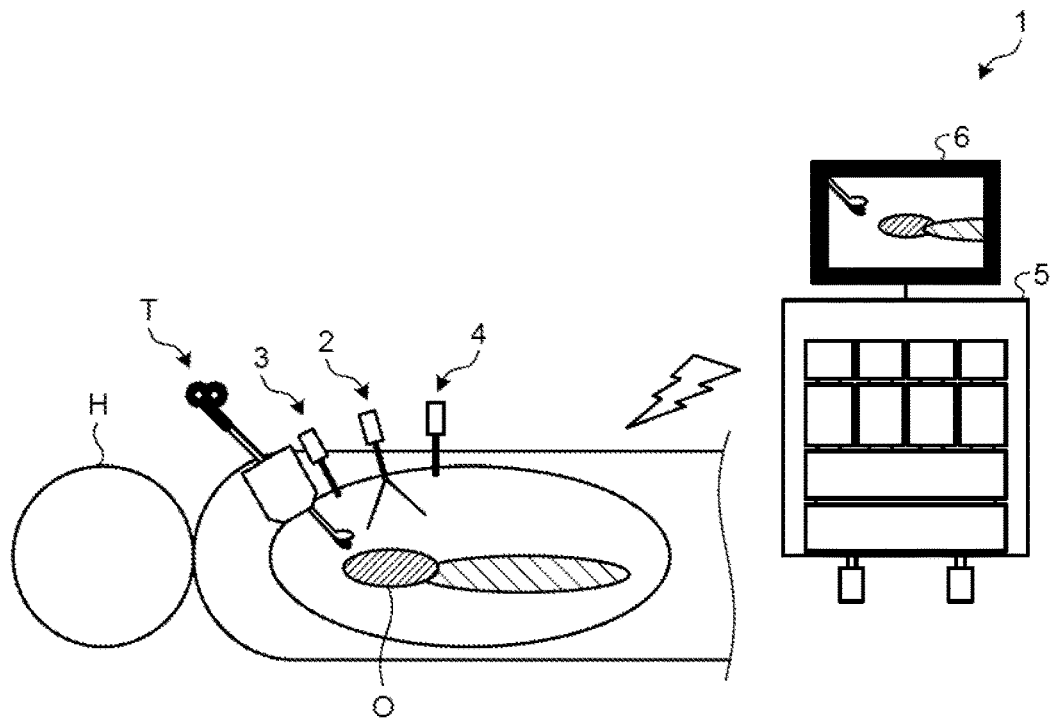
FIG. 1 is a schematic view illustrating a configuration of an observation system according to a first embodiment.

Preferred embodiments of an image processing apparatus, an observation system, and an observation method according to the disclosure will be explained below with reference to accompanying drawings. Furthermore, the disclosure is not limited to the embodiments below. The disclosure is applicable to an image processing apparatus, an observation system, and an observation method that are typically used and that use a plurality of imagers that capture images of an observation target located inside a subject at different positions from each other.

Furthermore, in the descriptions of the drawings, components that are identical or corresponding to those in embodiments are appropriately denoted by the same reference numerals. In addition, it is necessary to note that the drawings used for the descriptions below are only schematic illustrations and the relationship of the size among the components, the ratios of the components, and the like may be different from those used in practice. Moreover, the drawings may include portions in which the relationship of the size among the components and the ratios of the components may sometimes differ between the drawings.

First Embodiment

Configuration of Observation System

First, a configuration of an observation system will be described. FIG. 1 is a schematic view illustrating a configuration of the observation system according to a first embodiment. As illustrated in FIG. 1, an observation system 1 according to the first embodiment observes an observation target O located inside a subject H. With the observation system 1, an endoscopic operation is performed by observing the observation target O located inside the subject H and performing treatment on the subject H by using a treatment instrument T.

Figure 2:
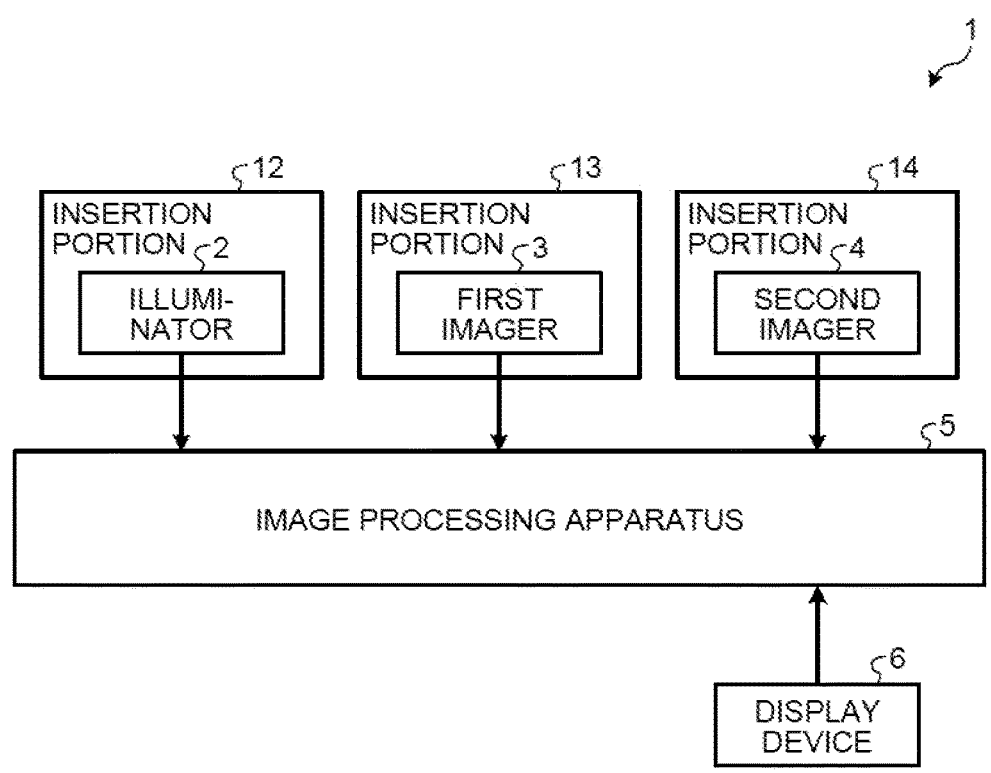
FIG. 2 is a block diagram illustrating a configuration of the observation system according to the first embodiment.

FIG. 2 is a block diagram illustrating a configuration of the observation system according to the first embodiment. As illustrated in FIG. 2, the observation system 1 includes an illuminator 2, a first imager 3, a second imager 4, an image processing apparatus 5, and a display device 6.

Figure 3:
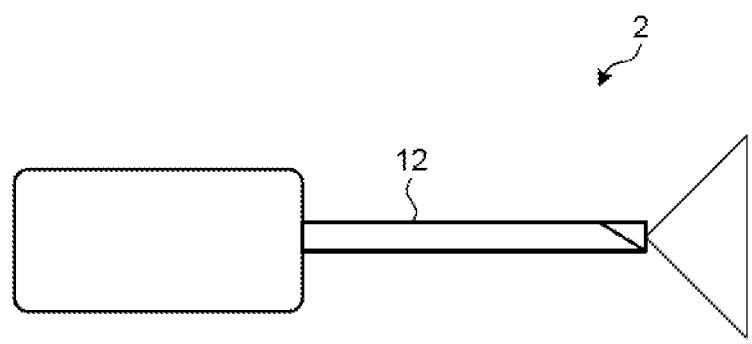
FIG. 3 is a schematic view illustrating a configuration of an illuminator.

The illuminator 2 irradiates the observation target O with illumination light. FIG. 3 is a schematic view illustrating a configuration of the illuminator. As illustrated in FIG. 3, the illuminator 2 is attached to the subject H by being inserted in an insertion portion 12 that is a rigid needle and is not bendable with a diameter between, for example, 2 mm and 3 mm, inclusive. A light source constituted of a light emitting diode (LED) or the like and a battery that supplies electrical power to the light source are provided on the side opposite to the insertion portion 12 that is included in the illuminator 2. The illumination light irradiated by the light source is irradiated onto the observation target O via a lens or an optical fiber that is disposed in an interior of the insertion portion 12. However, the illuminator 2 may irradiate the observation target O with illumination light that is output by an external light source device located outside.

The first imager 3 and the second imager 4 captures images of the observation target O from different positions from each other. In a description below, an example in which two imagers are provided is described; however, three or more imagers may be provided as long as a plurality of imagers are provided. Furthermore, in a description below, an image captured by the first imager 3 is referred to as a first image, whereas an image captured by the second imager 4 is referred to as a second image.

Figure 4:
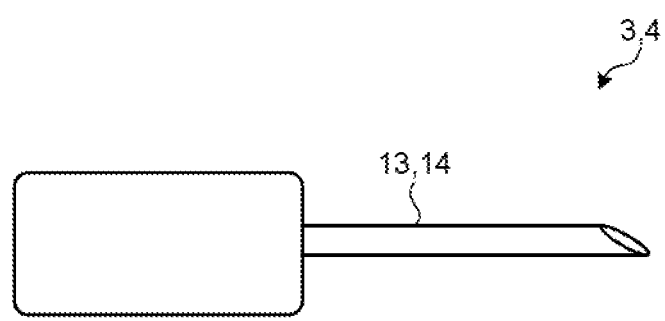
FIG. 4 is a schematic view illustrating a configuration of each of a first imager and a second imager.

FIG. 4 is a schematic view illustrating a configuration of each of the first imager and the second imager. As illustrated in FIG. 4, each of the first imager 3 and the second imager 4 is attached to the subject H by being inserted in an insertion portion 13 and an insertion portion 14, respectively, each of which is a rigid needle and is not bendable with a diameter between, for example, 2 mm and 3 mm, inclusive. As a result of the insertion portion 13 and the insertion portion 14 are punctured into the subject H at different positions from each other, the first imager 3 and the second imager 4 capture images of the observation target O at different positions from each other. An imaging element constituted by using an image sensor such as a charge coupled device (CCD) and a complementary metal oxide semiconductor (CMOS), and an A/D conversion circuit, and the like is provided on the side opposite to the insertion portion 13 and the insertion portion 14 that are included in the first imager 3 and the second imager 4, respectively. In addition, the light reflected from the observation target O is captured by the imaging element via a lens or an optical fiber that is disposed in the interior of each of the insertion portion 13 and the insertion portion 14.

Figure 5:
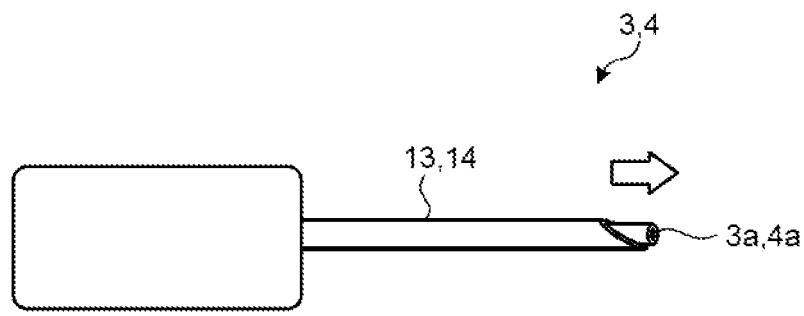
FIG. 5 is a diagram illustrating a state in which a distal end of each of the first imager and the second imager protrudes from a distal end of an insertion portion.

FIG. 5 is a diagram illustrating a state in which the distal end of each of the first imager and the second imager protrudes from the distal end of the associated insertion portion. As illustrated in FIG. 5, a distal end portion 3a and a distal end portion 4a of the first imager 3 and the second imager 4, respectively, may protrude from the distal end of the insertion portion 13 and the insertion portion 14, respectively. After the insertion portion 13 and the insertion portion 14 are punctured, by allowing the distal end portion 3a and the distal end portion 4a of the first imager 3 and the second imager 4, respectively, to project from the distal ends of the insertion portion 13 and the insertion portion 14, respectively, it is possible to prevent a stain, such as a body fluid, from being adhered to the distal end of the first imager 3 and the second imager 4, respectively. Similarly, the illuminator 2 may be configured such that the distal end portion of the illuminator 2 is able to protrude from the distal end of the insertion portion 12.

Figure 6:
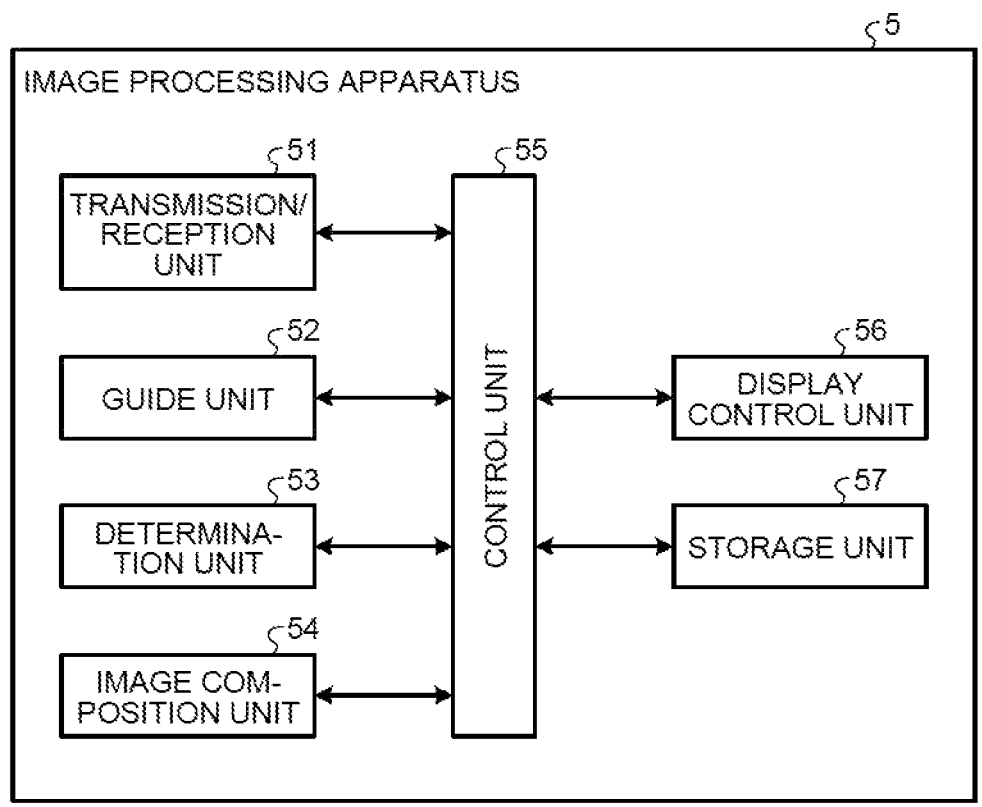
FIG. 6 is a block diagram illustrating a configuration of an image processing apparatus according to the first embodiment.

FIG. 6 is a block diagram illustrating a configuration of the image processing apparatus according to the first embodiment. As illustrated in FIG. 6, the image processing apparatus 5 includes a transmission/reception unit 51, a guide unit 52, a determination unit 53, an image composition unit 54, a control unit 55, a display control unit 56, and a storage unit 57.

The transmission/reception unit 51 performs communication with an external device, such as the illuminator 2, the first imager 3, and the second imager 4, in a wired or wireless manner and transmits and receives various signals.

The guide unit 52 guides a position of each of the first imager 3 and the second imager 4. The guide unit 52 guides a position at which each of the first imager 3 and the second imager 4 is to be punctured or a positional relationship between a position of the observation target O and positions of the first imager 3 and the second imager 4 by performing a voice output, outputting characters to the display device 6, irradiating the subject H with light, or the like. The guide unit 52 may guide the position of each of the first imager 3 and the second imager 4 to the in-focus position, or may guide such that the observation target O is included by a ratio equal to or larger than a predetermined ratio. The guide unit 52 is constituted by using a general purpose processor, such as a central processing unit (CPU), or a special purpose processor, such as various arithmetic circuits including an application specific integrated circuit (ASIC), that executes a specific function.

The determination unit 53 determines whether or not an overlapping portion is present in an imaging area included in the first image captured by the first imager 3 that captures an image of the observation target O located inside the subject H and the second image captured by the second imager 4 that captures the observation target O at a position different from a position at which the first imager 3 captures the image of the observation target O. Furthermore, the determination unit determines whether or not each of the first imager 3 and the second imager 4 is inserted to a focal point position. The focal point position mentioned here is used for an explanation of a position at which the first imager 3 or the second imager 4 is disposed at a distance at which the observation target O is in focus. This is because that, at the time of determination of a state of an image of the observation target O during the process of insertion, if the first imager 3 or the second imager 4 included in the imaging optical system is located out of focus, an image is blurred and a contrast is thus decreased; however, a contrast is favorable in an in-focus state (focal point position), so that detection is possible based on a change in contrast or a comparison with a predetermined value. These can be determined by obtaining a contrast value of the image by the image processing apparatus 5. The determination unit 53 is implemented by a general purpose processor, such as a CPU, or a special purpose processor, such as an ASIC including various arithmetic circuits, that performs a specific function.

If the determination unit 53 determines that each of the first imager 3 and the second imager 4 is inserted to the focal point position at which the observation target O is in focus and determines that an overlapping portion is present in both of the imaging area included in the first image and the imaging area included in the second image, the image composition unit 54 generates a composite image that is composed of the first image and the second image. The image composition unit 54 is implemented by a general purpose processor, such as a CPU, or a special purpose processor, such as an ASIC including various arithmetic circuits, that performs a specific function.

The control unit 55 performs control of the entire operation process performed by the observation system 1. The control unit 55 is implemented by a general purpose processor, such as a CPU, or a special purpose processor, such as an ASIC including various arithmetic circuits, that performs a specific function. Furthermore, a configuration of all or some of the guide unit 52, the determination unit 53, the image composition unit 54, the control unit 55, and the display control unit 56 may be implemented by a single processor, such as a CPU.

The display control unit 56 controls a display of the display device 6 by causing the display device 6 to display various screens. The display control unit 56 is implemented by a general purpose processor, such as a CPU, or a special purpose processor, such as an ASIC including various arithmetic circuits, that performs a specific function.

The storage unit 57 stores therein an execution program, a control program, and a parameter, such as a threshold, for the control unit 55 executing various operations. The control unit 55 is constituted by a volatile memory and a non-volatile memory, or a combination thereof. Specifically, the control unit 55 is constituted by a random access memory (RAM), a read only memory (ROM), or the like.

The display device 6 displays various screens under the control of the display control unit 56. The display device 6 may be a monitor having a display unit, such as a liquid crystal display, an organic electro luminescence (EL) display, or may be a head mounted display that is able to be worn on the head of an operator, such as a doctor.

Observation Method Performed by Using Observation System

Figure 7:
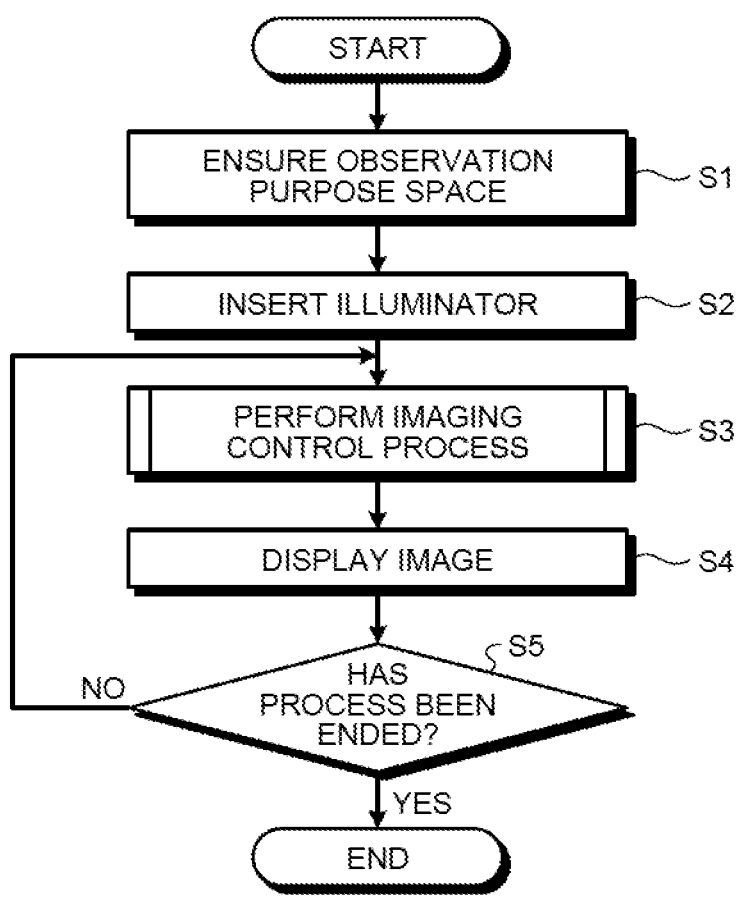
FIG. 7 is a flowchart illustrating an outline of a process performed by the observation system according to the first embodiment.

In the following, an observation method of the subject H performed by using the observation system 1 will be described. FIG. 7 is a flowchart illustrating an outline of a process performed by the observation system according to the first embodiment. As illustrated in FIG. 7, an observation purpose space for observing the observation target O located in the inside of the subject H is ensured (Step S1: a space securing step). Specifically, an abdominal cavity is expanded by injecting carbonic acid gas into the abdominal cavity of the subject H and ensures the observation purpose space. Furthermore, the observation purpose space may be ensured by pulling a surface skin of the subject H.

Subsequently, the illuminator 2 is inserted into the subject H (Step S2). Specifically, the illuminator 2 is inserted into the subject H by puncturing the insertion portion 12, in which the illuminator 2 is inserted, into the subject H. The insertion portion 12 is not bent, so that the carbonic acid gas injected into the abdominal cavity of the subject H is less likely to leak even if the insertion portion 12 is inserted into the subject H. At this time, the guide unit 52 may guide the position at which the insertion portion 12, in which the illuminator 2 is inserted, is to be punctured into the subject H. Specifically, the guide unit 52 guides a puncture site by outputting a voice or by projecting a marker that indicates the puncture site on the body surface of the subject H.

Figure 8:
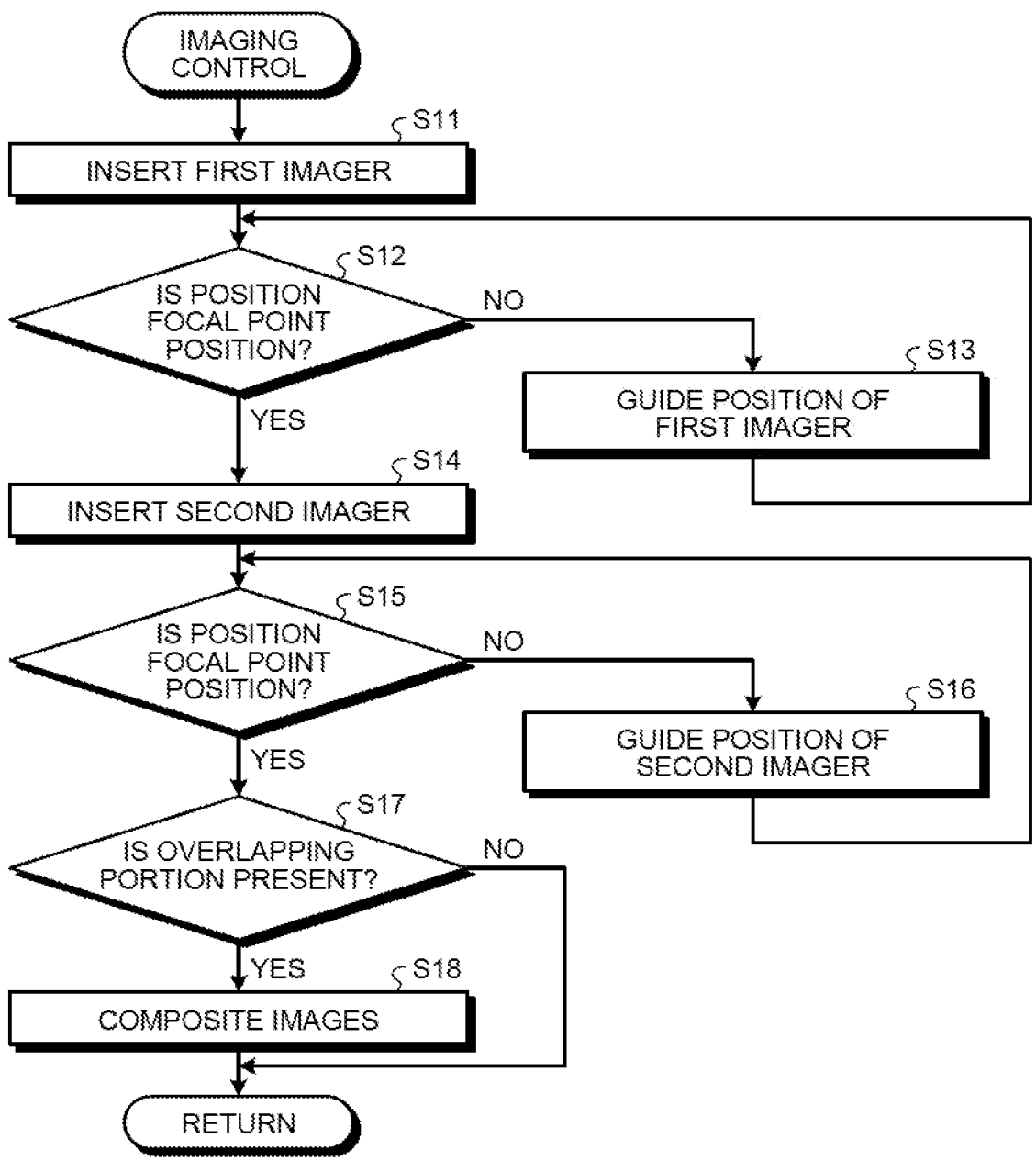
FIG. 8 is a flowchart illustrating an outline of an imaging control process illustrated in FIG. 7.

Then, the image processing apparatus 5 performs an imaging control process (Step S3). FIG. 8 is a flowchart illustrating an outline of the imaging control process illustrated in FIG. 7. As illustrated in FIG. 8, the first imager 3 that captures an image of the observation target O is inserted into the subject H (Step S11: a first insertion step). Specifically, the first imager 3 is inserted into the subject H by puncturing the insertion portion 13, in which the first imager 3 is inserted, into the subject H. The insertion portion 13 is not bent, so that the carbonic acid gas injected into the abdominal cavity of the subject H is less likely to leak even if the insertion portion 13 is inserted into the subject H. At this time, the guide unit 52 may guide the position at which the insertion portion 13, in which the first imager 3 is inserted, is to be punctured into the subject H. Specifically, the guide unit 52 guides the puncture site by outputting a voice or by projecting a marker that indicates the puncture site on the body surface of the subject H.

Subsequently, the determination unit 53 determines whether or not the first imager 3 is inserted to the focal point position at which the observation target O is in focus (Step S12). Specifically, the determination unit 53 acquires, via the transmission/reception unit 51, a signal of the first image captured by the first imager 3, and determines, by using the signal of the first image, whether or not the first imager 3 is inserted to the focal point position.

Figure 9:
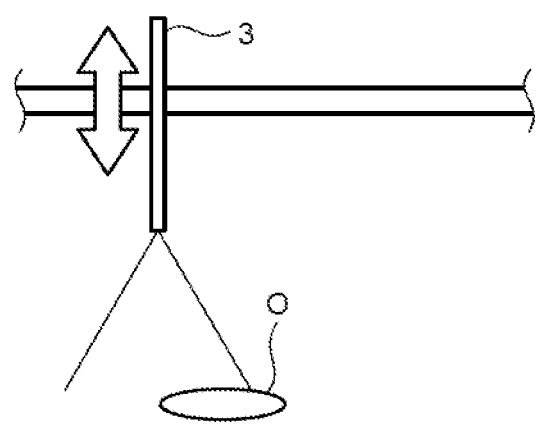
FIG. 9 is a diagram illustrating a state in which the first imager is guided.

Here, if the determination unit 53 determines that the first imager 3 is not inserted to the focal point position (No at Step S12), the guide unit 52 guides the position of the first imager 3 (Step S13). FIG. 9 is a diagram illustrating a state in which the first imager is guided. As illustrated in FIG. 9, in order to make a distance between the first imager 3 and the observation target O to be an appropriate distance, the guide unit 52 guides the position of the first imager 3 by outputting a message, such as "Please move closer." or "Please move farther away." by a voice. However, the guide unit 52 may guide the position of the first imager 3 by displaying the message on the display device 6 using characters.

Figure 10:
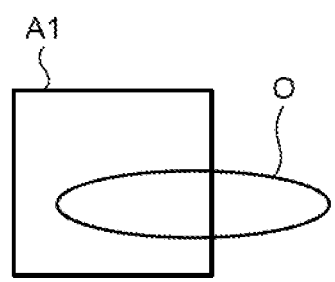
FIG. 10 is a diagram illustrating an example of an image captured by the first imager.

FIG. 10 is a diagram illustrating an example of an image captured by the first imager. As illustrated in FIG. 10, the first imager 3 is inserted to the focal point position by being guided by the guide unit 52. At this time, it is assumed that a part of the observation target O is included in an imaging area A1 captured by the first imager 3.

Then, if the determination unit 53 determines that the first imager 3 is inserted to the focal point position (Yes at Step S12), the second imager 4 is inserted into the subject H (Step S14: a second insertion step). Specifically, by puncturing the insertion portion 14, in which the second imager 4 is inserted, to position that is different from a position of the insertion portion 13 in the subject H, the second imager 4 that captures an image of the observation target O at a position that is different from a position at which the first imager 3 captures the image of the observation target O is inserted into the subject H. The insertion portion 14 is not bent, the carbonic acid gas injected into the abdominal cavity of the subject H is less likely to leak even if the insertion portion 14 is inserted into the subject H. At this time, the guide unit 52 may guide the position at which the insertion portion 14, in which the second imager 4 is inserted, is to be punctured into the subject H. Specifically, the guide unit 52 guides the puncture site by outputting a voice, by projecting a marker that indicates the puncture site on the body surface of the subject H, or the like. Furthermore, here, a description has been made with the assumption that the second imager 4 is inserted; however, as illustrated in FIG. 10, although a part of the observation target O is included in the imaging area A1 captured by the first imager 3, if the entire of the observation target O is not able to be captured, the guide unit 52 may guide, by using a voice, characters, or the like, a desirable alternative indicating that it is preferable that the second imager 4 is inserted in order to generate a composite image including the entire of the observation target O.

Subsequently, the determination unit 53 determines whether or not the second imager 4 is inserted to the focal point position in which the observation target O is in focus (Step S15). Specifically, the determination unit 53 acquires, via the transmission/reception unit 51, a signal of the second image captured by the second imager 4 and determines, by using the acquired signal of the second image, whether or not the second imager 4 is inserted to the focal point position.

Figure 11:
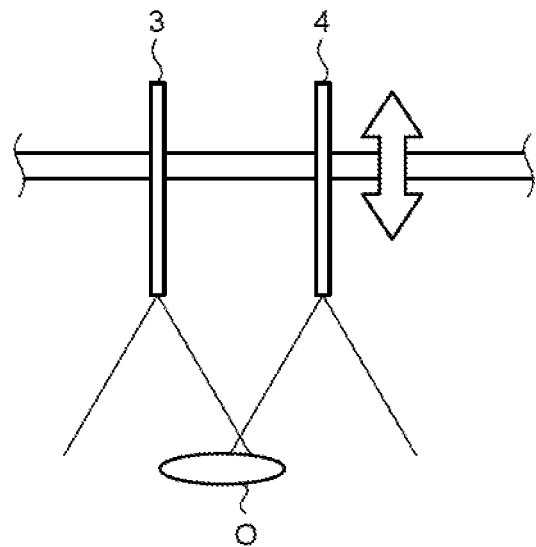
FIG. 11 is a diagram illustrating a state in which the second imager is guided.

Here, if the determination unit 53 determines that the second imager 4 is not inserted to the focal point position (No at Step S15), the guide unit 52 guides the position of the second imager 4 (Step S16). FIG. 11 is a diagram illustrating a state in which the second imager is guided. As illustrated in FIG. 11, in order to make the distance between the second imager 4 and the observation target O to be an appropriate distance, the guide unit 52 guides the position of the second imager 4 by outputting, by a voice, a message, such as "Please move closer." or "Please move farther away.". However, the guide unit 52 may guide the position of the second imager 4 by displaying the message on the display device 6 using characters.

If the second imager 4 is inserted to focal point position on the basis of the guide performed by the guide unit 52 and if the determination unit 53 determines that the second imager 4 is inserted to the focal point position (Yes at Step S15), the determination unit 53 determines whether or not an overlapping portion is present in the imaging area of the first image captured by the first imager 3 and the imaging area of the second image captured by the second imager 4 (Step S17: determination step). Specifically, the determination unit 53 determines whether or not an overlapping portion is present by extracting, by performing image processing, a feature point (a point characteristic of an image, such as an end portion of a lesion or a bleeding point) included in the first image and a feature point included in the second image and comparing the positions of the feature points with each other.

If the determination unit 53 determines that an overlapping portion is present in the imaging area of the first image and the imaging area of the second image (Yes at Step S17), the image composition unit 54 composites the first image and the second image (Step S18: image composition step). In this way, in the first embodiment, it is possible to provide the image processing apparatus 5 that includes the determination unit 53 that determines whether or not an overlapping portion is present in the imaging area of the first image and the imaging area of the second image that are captured by the first imager 3 and the second imager 4, respectively, that are inserted into the subject H to capture the observation target O at different positions from each other and that determines whether or not each of the first imager 3 and the second imager 4 is inserted to the focal point position, and includes the image composition unit 54 that generates a composite image that is composed of the first image and the second image when the determination unit 53 determines that each of the first imager 3 and the second imager 4 is inserted to the focal point position and determines that an overlapping portion is present in the imaging area of the first image and the imaging area of the second image. Here, a case in which two images are composed has been described; however, the contents described in the present application is assumed in a case in which, in addition to the case in which the two images are composed, a third image and a fourth image are further composed with a plurality of (two or more) images. Furthermore, the flowchart illustrated in FIG. 8 indicates an example in which determination is performed in series; however, composition may be performed, by always detecting a focusing state (whether or not each of the first imager 3 and the second imager 4 is inserted to the focal point position), when both focuses are in focus or out of focus, or are in a similar focus state. By doing so, an operator, such as a doctor, is able to concentrate an operation for inserting the first imager 3 and the second imager 4.

Figure 12:
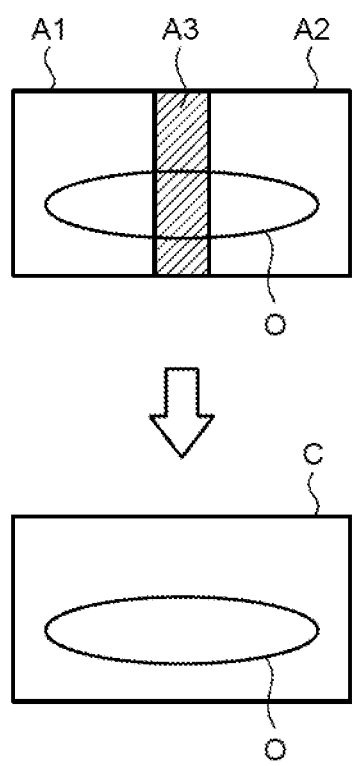
FIG. 12 is a diagram illustrating a state in which images are composed.

FIG. 12 is a diagram illustrating a state in which images are composed. As illustrated in FIG. 12, if an overlapping area A3 is present in the imaging area A1 included in the first image and the imaging area A2 included in the second image, the image composition unit 54 generates a composite image C that is composed of the first image and the second image. The entire of the observation target O is included in the composite image C. After that, the imaging control process is ended, and the process proceeds to Step S4 illustrated in FIG. 7. Furthermore, in the first embodiment, it may design a method of preventing the composite image C from being unsuitable image caused by illumination unevenness. In other words, in addition to the determination whether or not "each of the first imager 3 and the second imager 4 is inserted to the focal point position" performed at Step S12 or Step S15 illustrated in FIG. 8, the determination unit 53 may perform determination "whether or not uniform illumination is obtained". Alternatively, even if the brightness of the entire of each of the first image and the second image is not uniform, if the brightness of a portion of the composite image C to be used is uniform or has an appropriate brightness distribution, the images are easily composed and it is possible to make a joint line occurred after the composition unnoticeable. This may be adjusted by the brightness of the illumination light irradiated from the illuminator 2 or may be adjusted by a distribution of light (what amount of light is to be irradiated from the illuminator 2 in which direction), or may be adjusted by the light receiving sensitivity of the first imager 3 and the second imager 4 or image processing performed in the image processing apparatus 5. In other words, it is possible to provide the image processing apparatus 5 that includes the determination unit 53 that determines whether or not an overlapping portion is present in the imaging area A1 included in the first image captured by the first imager 3 that captures the irradiated observation target O that is located inside the subject H and that is a portion of composition and the imaging area A2 included in the second image captured by the second imager 4 that captures the observation target O at a position that is different from a position at which the first imager 3 captures the irradiated observation target O, and the image composition unit 54 that generates a composite image that is composed of the first image and the second image by reducing brightness unevenness of the overlapping portion when the determination unit 53 determines that the overlapping portion is present. Here, a case in which two images are composed has been described; however, the contents described in the present application is assumed in a case in which, in addition to the case in which two images are composed, a third image and a fourth image are further composed with a plurality of (two or more) images. The flowchart illustrated in FIG. 8 indicates an example in which determination is performed in series; however, composition may be performed, by always detecting an illumination state, when the level of the brightness unevenness of the composite portion of both of the images is equal to or less than a predetermined value. By doing so, an operator, such as a doctor, is able to concentrate an operation for inserting the illuminator 2.

At Step S17, if the determination unit 53 determines that an overlapping portion is not present in the imaging area of the first image and imaging area of the second image (No at Step S17), the determination unit 53 ends the imaging control process and proceeds to Step S4 illustrated in FIG. 7.

Subsequently, the display control unit 56 causes the display device 6 to display an image (Step S4). Specifically, if the composite image C has been generated, the display control unit 56 causes the display device 6 to display the composite image C. In contrast, if the composite image C is not generated, the display control unit 56 causes the display device 6 to display the first image and the second image in parallel. At this time, the display control unit 56 may allow the first image and the second image to be displayed such that positional relationship in the inside of the subject H is indicated.

Then, the control unit 55 determines whether or not an operation for ending the series of the processes has been input (Step S5), and, if the control unit 55 determines that this operation has been input (Yes at Step S5), the series of the operations are ended. In contrast, if the control unit 55 determines that this operation has not been input (No at Step S5), the process returns to Step S3 and will be continued.

According to the first embodiment described above, by generating the composite image C that is composed of the first image and the second image, it is possible to observe the entire of the observation target O that is not able to be captured by only the first imager 3. Accordingly, according to the observation system 1, it is possible to sufficiently ensure a field of view in an endoscopic operation.

Furthermore, in the first embodiment, the diameter of the insertion portion 12, the insertion portion 13, and the insertion portion 14 that include the illuminator 2, the first imager 3, and the second imager 4, respectively, is equal to or less than 3 mm. In general, if the diameter of a needle is equal to or less than 3 mm, an incision is not left on the subject H, so that, according to the observation system 1, it is possible to perform an endoscopic operation such that an incision is not left on the subject H. In contrast, the diameter of a rigid endoscope or a trocar that is used in a conventional endoscopic operation is mainly 5 mm or 10 mm and is less invasiveness when compared to that used in an abdominal operation, but an incision is left on the subject H.

Furthermore, the conventional endoscope system (for example, a rigid endoscope or an endoscope system, such as a surgery support robot, with an outer diameter of 5 mm or 10 mm) may be used together with the illuminator 2, the first imager 3, and the second imager 4. For example, it may be possible to observe in the interior of the subject H using the rigid endoscope that is inserted by using a trocar and observe, in a secondary manner, in the interior of the subject H using the illuminator 2, the first imager 3, and the second imager 4. In this case, similarly to the conventional endoscope system, an incision made by the trocar is left; however, an incision made by an auxiliary observation that is additionally performed is not left, so that it is possible to safely carry out an operation while obtaining a large amount of information without further increasing invasiveness than that exhibited in the conventional endoscopic operation.

Furthermore, in the first embodiment, a case has been described as an example in which two imagers of the first imager 3 and the second imager 4 are used; however, it is possible to expand the field of view by using three or more imager. Furthermore, if an un-imaged portion is present in the observation target O, it is possible to prevent an occurrence of a blind angle such that the guide unit 52 instructs to add an imager. In this way, by using the plurality of imagers, it is possible to arbitrarily expand a field of view without leaving an incision on the subject H. In a conventional endoscopic operation, it is difficult to freely ensure a field of view; however, according to the first embodiment, it is possible to ensure a field of view requested by an operator with less invasiveness. Furthermore, a 3D image may be generated by capturing images of the observation target O from various angles by using the plurality of imagers. By generating the 3D image, the operator performs observation more easily without leaving an incision on the subject H.

Furthermore, in the first embodiment, it is possible to enhance image quality by overlapping the imaging areas included in the first image and the second image, it is possible to change a depth of a site to be observed by changing the depth of the first imager 3 and the second imager 4 inserted into the subject H, it is possible to change an area to be observed by removing the first imager 3 and the second imager 4 from the subject H and again puncturing the subject H, and it is possible to add information obtained by additionally performing a puncturing operation by using a new imager. According to the first embodiment, it is possible to observe the interior of the subject H in a less invasiveness manner even if these field of views are changed.

Furthermore, in the first embodiment, the first imager 3 and the second imager 4 complement with each other, so that high performance (high image quality, high frame rate, etc.) is not needed for a single function performed by each of the illuminators. As a result, it is easy to manufacture these imagers at low cost. Furthermore, high performance is not needed for the first imager 3 and the second imager 4, so that it is possible to reduce an effect on the subject H caused by heat generated at the time of use, and it is also possible to increase durability of the first imager 3 and the second imager 4 themselves.

Furthermore, in the first embodiment described above, a case has been described as an example in which the image processing apparatus 5 controls the illuminator 2, the first imager 3, and the second imager 4; however, it may be configured such that each of the illuminator 2, the first imager 3, and the second imager 4 may be controlled by a single processor. By allowing the processor to handle each of the units in a divisional manner, it is possible to manufacture a unit in which the illuminator 2, the first imager 3, and the second imager 4 are associated with the processor. In addition, if a plurality of illuminators and a plurality of imagers are used, by using the plurality of units in combination, it is possible to easily expand the functions thereof.

Furthermore, in the first embodiment described above, a case has been described as an example in which the subject H corresponding to a single person is observed; however, a plurality of different subjects H may be observed by using the first imager 3 and the second imager 4. In other words, by using a combination of the above described illuminator or imager and the processor as a unit, it is possible to observe a single subject with a wide field of view and it is also possible to simultaneously observe a plurality of subjects.

Furthermore, in the first embodiment described above, it is determined whether or not an overlapping portion is present by comparing an imaging area of the first image to an imaging area of the second image, and then, the first image and the second image are composed; however, the embodiment is not limited to this. The first image and the second image may be composed by acquiring positional information on each of the first imager 3 and the second imager 4 by using a device, such as a camera that is used for position detection, a magnetic field sensor, or a cone beam computed tomography (CT) machine, and determining whether or not an overlapping portion is present on the basis of the positional information. Furthermore, if the camera for position detection is used, it is preferable that the first imager 3 and the second imager 4 are colored with colors that are easy to recognize, the first imager 3 and the second imager 4 are distinguishably colored, or an identification mark, such as a QR code (registered trademark) is provided. In addition, if the magnetic field sensor is used, it is preferable that each of the first imager 3 and the second imager 4 has a magnetic field generation device.

Furthermore, in the first embodiment described above, the image quality or the frame rate may be the same or different in the first imager 3 and the second imager 4. For example, in the case where a portion gazed at by the operator, such as the doctor, can be detected by using a technology, such as an eye-tracking technology, it may be possible to increase the image quality or the frame rate of the imager that captures an image of the gazed area. Furthermore, a load applied to a process performed by the image processing apparatus 5 may be reduced by decreasing the image quality or the frame rate of the imager that captures an image other than the gazed area.

Furthermore, in the first embodiment described above, a case has been described as an example in which the guide unit 52 gives an instruction to the operator by a voice or the like and guides the positions of the first imager 3 and the second imager 4; however, the embodiment is not limited to this. The guide unit 52 may guide the positions of the first imager 3 and the second imager 4 by transmitting an electromagnetic instruction to a robotic arm that operates the first imager 3 and the second imager 4.

Second Embodiment

Figure 13:
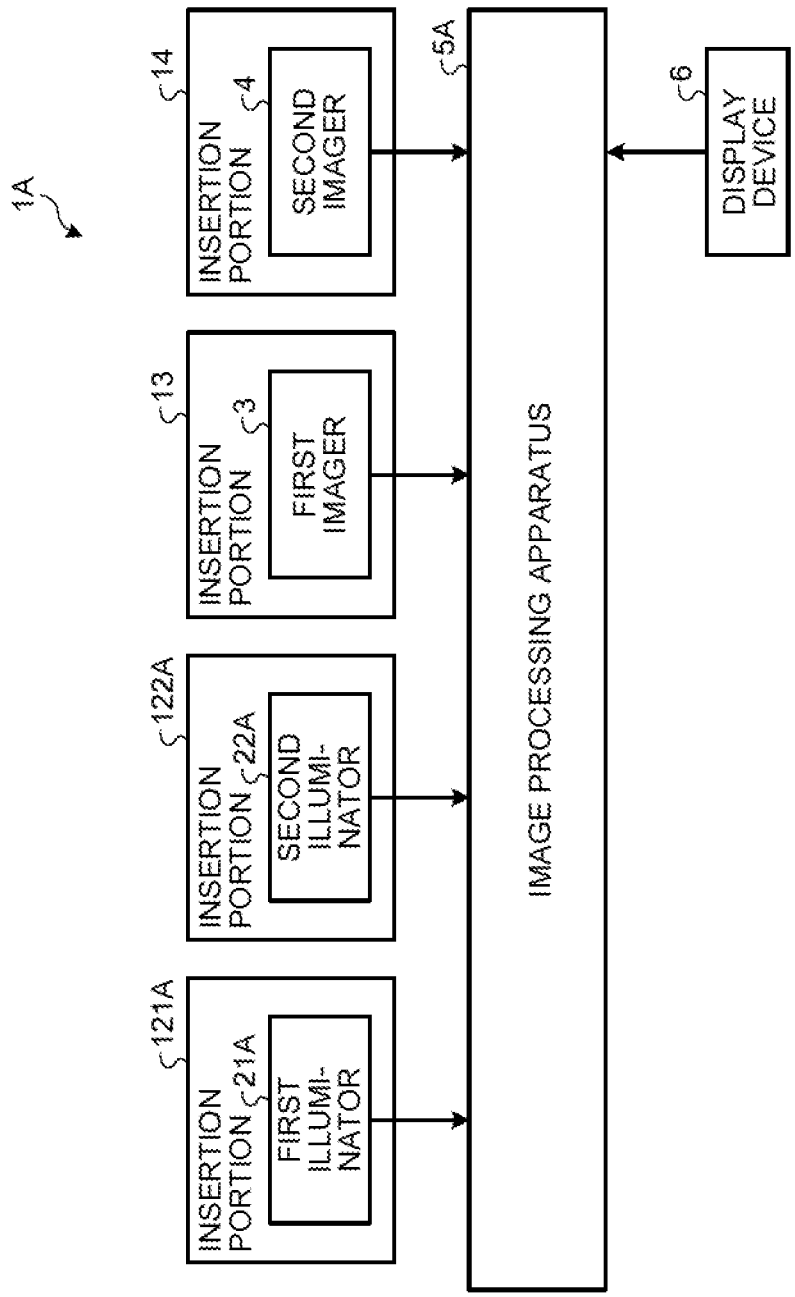
FIG. 13 is a block diagram illustrating a configuration of an observation system according to a second embodiment.

FIG. 13 is a block diagram illustrating a configuration of an observation system according to a second embodiment. An observation system 1A illustrated in FIG. 13 includes a first illuminator 21A, a second illuminator 22A, and an image processing apparatus 5A. The other configurations may be the same as those described in the first embodiment; therefore, descriptions thereof will be omitted.

The first illuminator 21A and the second illuminator 22A irradiates the observation target O with illumination light from different positions from each other. The first illuminator 21A and the second illuminator 22A are attached to the subject H by being inserted in an insertion portion 121A and an insertion portion 122A, respectively, each of which is a rigid needle and is not bendable with a diameter between, for example, 2 mm and 3 mm, inclusive. The configurations of the first illuminator 21A and the second illuminator 22A may be the same as that of the illuminator 2.

In other words, the first illuminator 21A and the second illuminator 22A are attached to the subject H by being inserted in the insertion portion 121A and the insertion portion 122A, respectively, that are punctured into the subject H at different positions from each other.

Figure 14:
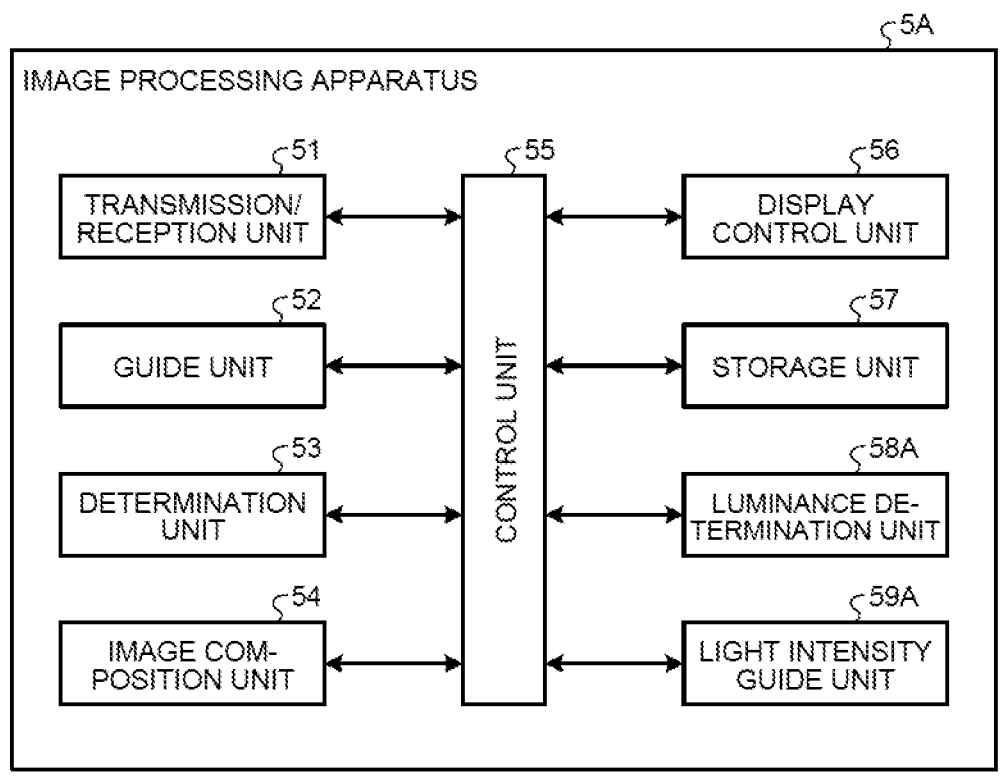
FIG. 14 is a block diagram illustrating a configuration of an image processing apparatus according to the second embodiment.

FIG. 14 is a block diagram illustrating a configuration of an image processing apparatus according to the second embodiment. As illustrated in FIG. 14, the image processing apparatus 5A includes a luminance determination unit 58A and a light intensity guide unit 59A.

The luminance determination unit 58A determines whether or not a luminance distribution is uniform in a composite image. The luminance determination unit 58A is implemented by a general purpose processor, such as a CPU, or a special purpose processor, such as an ASIC including various arithmetic circuits, that executes a specific function.

The light intensity guide unit 59A guides, on the basis of the determination result obtained by the luminance determination unit 58A, the position of the first illuminator 21A and the intensity of light irradiated by the first illuminator 21A onto the observation target O, and guides, on the basis of the determination result obtained by the luminance determination unit 58A, the position of the second illuminator 22A and the intensity of light irradiated onto the observation target O by the second illuminator 22A. By outputting a voice, outputting characters to the display device 6, irradiating the subject H with light, or the like, the light intensity guide unit 59A guides the first illuminator 21A and the second illuminator 22A to the position to be punctured, a positional relationship between positions of the first illuminator 21A and the second illuminator 22A and a position of the observation target O, and the intensity of light irradiated by the first illuminator 21A and the second illuminator 22A. The light intensity guide unit 59A is implemented by a general purpose processor, such as a CPU, or a special purpose processor, such as an ASIC including various arithmetic circuits, that executes a specific function.

Figure 15:
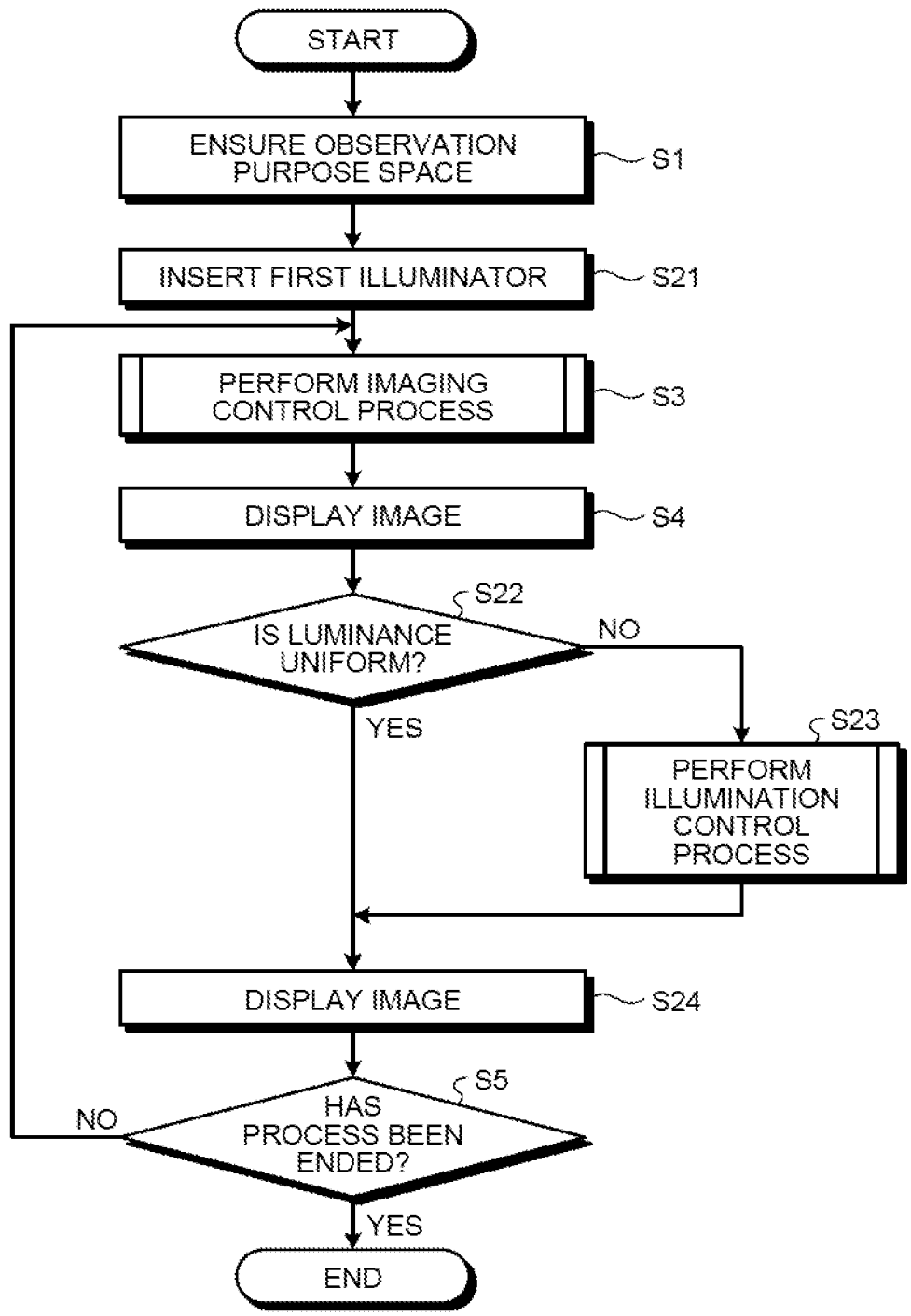
FIG. 15 is a flowchart illustrating an outline of a process performed by the observation system according to the second embodiment.
Figure 16:
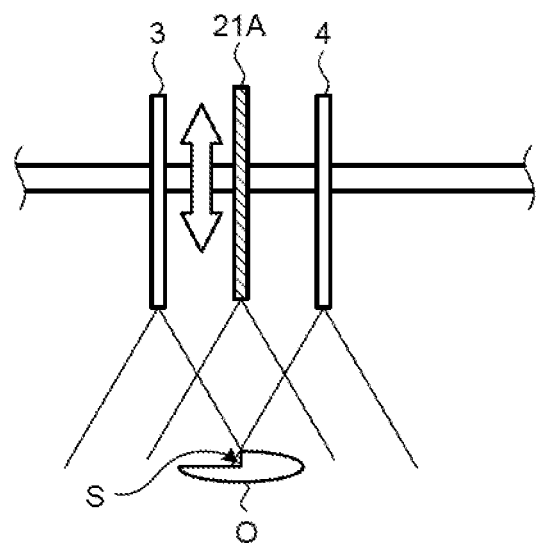
FIG. 16 is a diagram illustrating a state in which a first illuminator is guided.

FIG. 15 is a flowchart illustrating an outline of a process performed by an observation system according to the second embodiment. As illustrated in FIG. 15, after Step S1, the first illuminator 21A is inserted into the subject H (Step S21). Specifically, by puncturing the insertion portion 121A, in which the first illuminator 21A is inserted, into the subject H, the first illuminator 21A is inserted into the subject H. At this time, the light intensity guide unit 59A may guide the position of the first illuminator 21A and the intensity of light irradiated onto the observation target O by the first illuminator 21A. FIG. 16 is a diagram illustrating a state in which the first illuminator is guided. As illustrated in FIG. 16, in order to make the distance between the first illuminator 21A and the observation target O to be an appropriate distance, the light intensity guide unit 59A guides the position of the first illuminator 21A by outputting, by a voice, a message, such as "Please move closer." or "Please move farther away.". Furthermore, in order to make the first illuminator 21A to have an appropriate intensity of light to be irradiated on the observation target O, the light intensity guide unit 59A guides the intensity of light of the first illuminator 21A by outputting, by a voice, a message, such as "Please further increase the intensity of light." or "Please further decrease the intensity of light.". However, the light intensity guide unit 59A may guide the position of the first illuminator 21A by displaying the message on the display device 6 using characters.

After that, similarly to the first embodiment, after having performed the processes at Step S3 Step S4, the luminance determination unit 58A determines whether or not the luminance distribution of the composite image is uniform (Step S22).

If the luminance determination unit 58A determines that the luminance distribution of the composite image is uniform (Yes at Step S22), the luminance determination unit 58A proceeds to Step S5.

Figure 17:
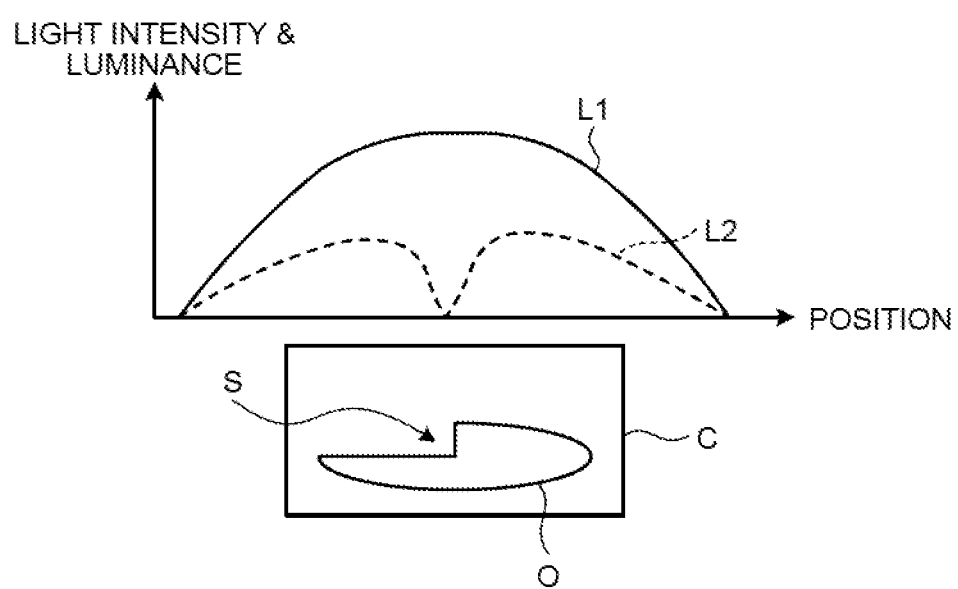
FIG. 17 is a diagram illustrating a luminance distribution in a composite image.

In contrast, if the luminance determination unit 58A determines that the luminance distribution of the composite image is not uniform (No at Step S22), the image processing apparatus 5 performs an illumination control process (Step S23). FIG. 17 is a diagram illustrating a luminance distribution in a composite image. A line L1 illustrated in FIG. 17 indicates the intensity of light irradiated onto the observation target O by the first illuminator 21A, whereas a line L2 indicates luminance of the composite image C. As illustrated in FIG. 17, if a step portion S is present on the observation target O and a dark portion is present at the central part of the composite image C, the luminance determination unit 58A determines that the luminance distribution is not uniform in the composite image C.

Figure 18:
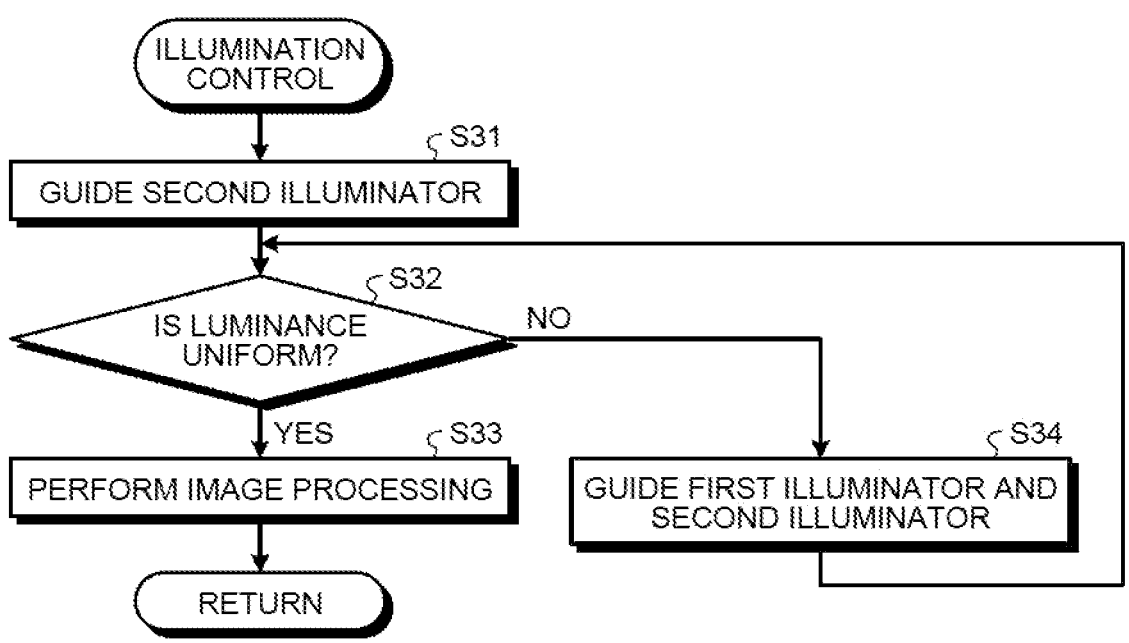
FIG. 18 is a flowchart illustrating an outline of the illumination control process illustrated in FIG. 15.
Figure 19:
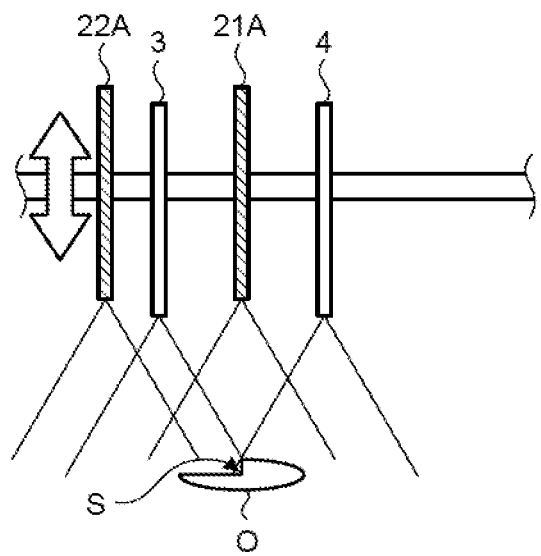
FIG. 19 is a diagram illustrating a state in which a second illuminator is guided.

FIG. 18 is a flowchart illustrating an outline of the illumination control process illustrated in FIG. 15. As illustrated in FIG. 18, in the illumination control process, the light intensity guide unit 59A guides, on the basis of the determination result obtained by the luminance determination unit 58A, the position of the second illuminator 22A and the intensity of light irradiated onto the observation target O by the second illuminator 22A (Step S31). FIG. 19 is a diagram illustrating a state in which the second illuminator is guided. As illustrated in FIG. 19, in order to make the distance between the second illuminator 22A and the observation target O to be an appropriate distance, the light intensity guide unit 59A guides the position of the second illuminator 22A by outputting, by a voice, a message, such as "Please move closer." or "Please move farther away.". Furthermore, in order to make the intensity of light to be irradiated onto the observation target O by the second illuminator 22A to be an appropriate intensity of light, the light intensity guide unit 59A guides the intensity of light emitted from the second illuminator 22A by outputting, by a voice, a message, such as "Please further increase the intensity of light." or "Please further decrease the intensity of light.". However, the light intensity guide unit 59A may guide the position of the second illuminator 22A by displaying the message on the display device 6 using characters.

Figure 20:
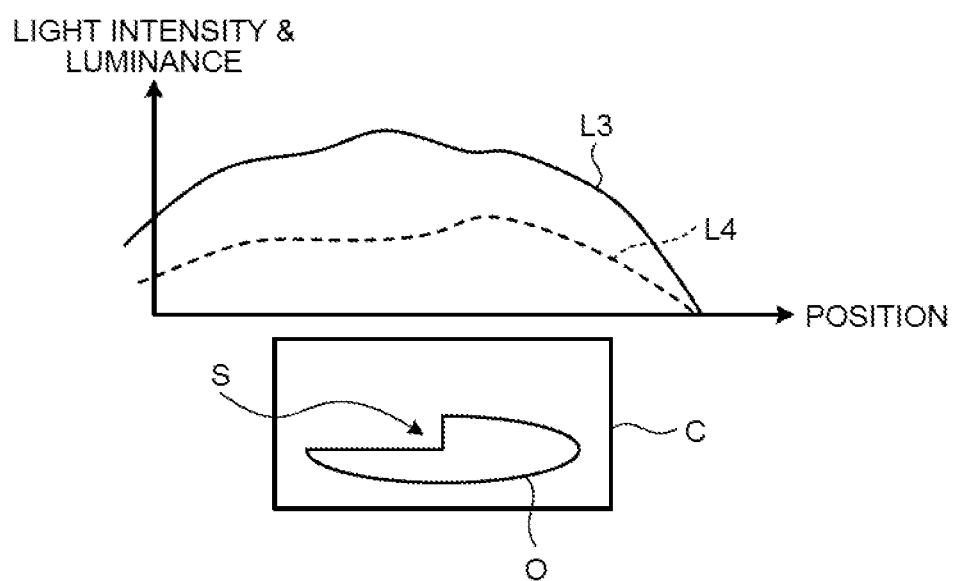
FIG. 20 is a diagram illustrating a luminance distribution in a composite image.

Subsequently, the luminance determination unit 58A determines whether or not the luminance distribution is uniform in the composite image C (Step S32). FIG. 20 is a diagram illustrating a luminance distribution in a composite image. As illustrated in FIG. 20, if light received from the second illuminator 22A is irradiated onto the step portion S included in the composite image C and a dark portion is not present in the composite image C, the luminance determination unit 58A determines that the luminance distribution is uniform in the composite image.

If the luminance determination unit 58A determines that the luminance distribution is uniform in the composite image C (Yes at Step S2), the image processing apparatus 5 performs image processing (Step S33). Specifically, the image processing apparatus 5 performs image processing that further uniform brightness of the entire of the composite image.

After that, the process proceeds Step S24 illustrated in FIG. 15, and the display control unit 56 causes the display device 6 to display the image (Step S24).

In contrast, at Step S22, if the luminance determination unit 58A determines that the luminance distribution is not uniform in the composite image (No at Step S22), the light intensity guide unit 59A guides the position of each of the first illuminator 21A and the second illuminator 22A and the intensity of light to be irradiated onto the observation target O by each of the first illuminator 21A and the second illuminator 22A (Step S34). After that, the process returns to Step S32 and the process will be continued.

According to the second embodiment described above, by inserting each of the first illuminator 21A and the second illuminator 22A into the subject H, it is possible to prevent a blind angle from occurring in the step portion S included in the observation target O and it is possible to sufficiently ensure a field of view.

Furthermore, in the second embodiment, the diameter of the insertion portion 121A and the insertion portion 122A included in the first illuminator 21A and the second illuminator 22A, respectively, is equal to or less than 3 mm, so that it is possible to perform an endoscopic operation such that an incision is not left on the subject H.

Furthermore, in the second embodiment, a case has been described as an example in which two illuminators corresponding to the first illuminator 21A and the second illuminator 22A are used; however, it may be possible to further adjust the intensity of light by using three or more illuminators. Furthermore, if a dark portion is present in the composite image C, it may be possible to prevent a blind angle from occurring in the composite image C by outputting an instruction to add an illuminator by the light intensity guide unit 59A.

Furthermore, in the second embodiment, it is possible to observe the observation target O in a brighter condition by overlapping irradiation areas of the illumination light irradiated by the first illuminator 21A and the second illuminator 22A, it is possible to change a depth of a site to be irradiated with illumination light by changing the depth of the first illuminator 21A and the second illuminator 22A inserted into the subject H, and it is possible to change an area to be irradiated with the illumination light by removing the first illuminator 21A and the second illuminator 22A from the subject H and again puncturing into the subject H. According to the second embodiment, it is possible to observe the interior of the subject H in a less invasiveness manner even if these illumination areas are changed.

Furthermore, in the second embodiment, the first illuminator 21A and the second illuminator 22A complement with each other, so that high luminance is not needed for a single function performed by each of the illuminators. As a result, it is easy to manufacture these illuminators at low cost. Furthermore, high luminance is not needed for the first illuminator 21A and the second illuminator 22A, so that it is possible to reduce an effect on the subject H caused by heat generated at the time of use, and it is also possible to increase durability of the first illuminator 21A and the second illuminator 22A themselves.

Third Embodiment

Figure 21:
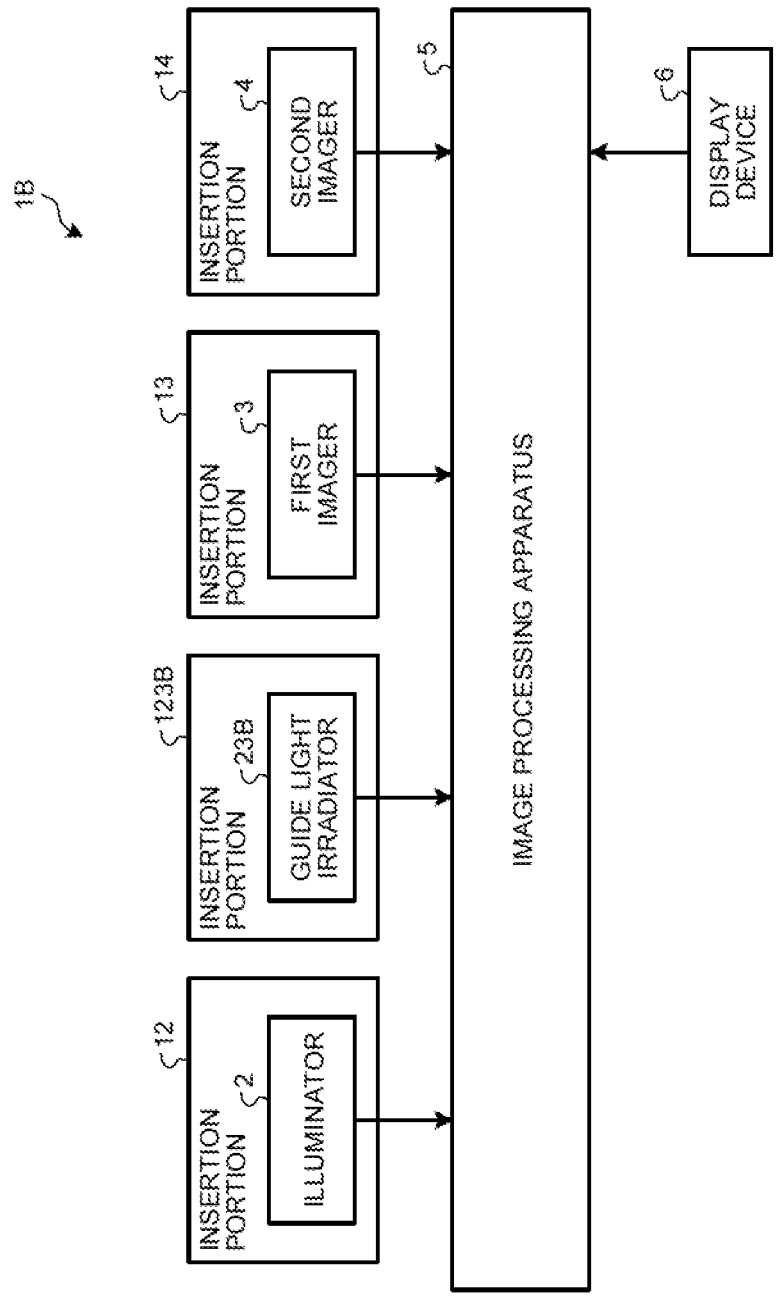
FIG. 21 is a block diagram illustrating a configuration of an observation system according to a third embodiment.

FIG. 21 is a block diagram illustrating a configuration of an observation system according to a third embodiment. As illustrated in FIG. 21, an observation system 1B includes a guide light irradiator 23B. The other configurations may be the same as those described in the first embodiment; therefore, descriptions thereof will be omitted.

The guide light irradiator 23B irradiates the observation target O with guide light. The guide light irradiator 23B is attached to the subject H by being inserted in an insertion portion 123B that punctures the subject H. The insertion portion 123B is a rigid needle and is not bendable with a diameter between, for example, 2 mm and 3 mm, inclusive. A light source constituted by an LED or the like and a battery that supplies electrical power to the light source are provided on the side opposite to the insertion portion 123B of the guide light irradiator 23B. The guide light emitted by the light source is irradiated onto the observation target O via a lens or an optical fiber that is disposed in an inside of the insertion portion 12. However, the illuminator 2 may irradiate the illumination light that is output by an external light source device onto the observation target O. The guide light is, for example, laser light having a random pattern, but may have a geometric pattern, such as lattice lines.

The determination unit 53 determines whether or not an overlapping portion is present in an imaging area included in each of the first image and the second image by comparing the guide light on the first image and the second image that are captured by the first imager 3 and the second imager 4, respectively.

The image composition unit 54 compares the guide light on the first image and the second image that are captured by the first imager 3 and the second imager 4, respectively, and generates a composite image that is composed of the first image and the second image.

Figure 22:
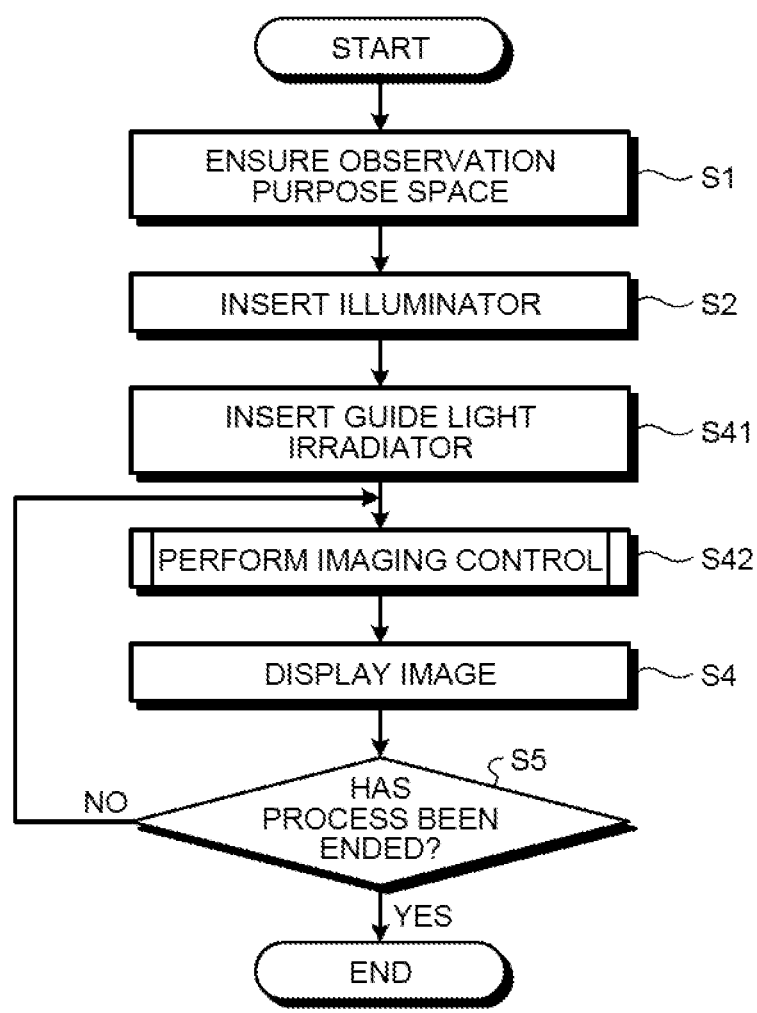
FIG. 22 is a flowchart illustrating an outline of a process performed by the observation system according to the third embodiment.

FIG. 22 is a flowchart illustrating an outline of a process performed by an observation system according to the third embodiment. As illustrated in FIG. 22, after Step S2, the guide light irradiator 23B is inserted into the subject H (Step S41). Specifically, the guide light irradiator 23B is inserted into the subject H by puncturing the insertion portion 123B, in which the guide light irradiator 23B is inserted, into the subject H.

Figure 23:
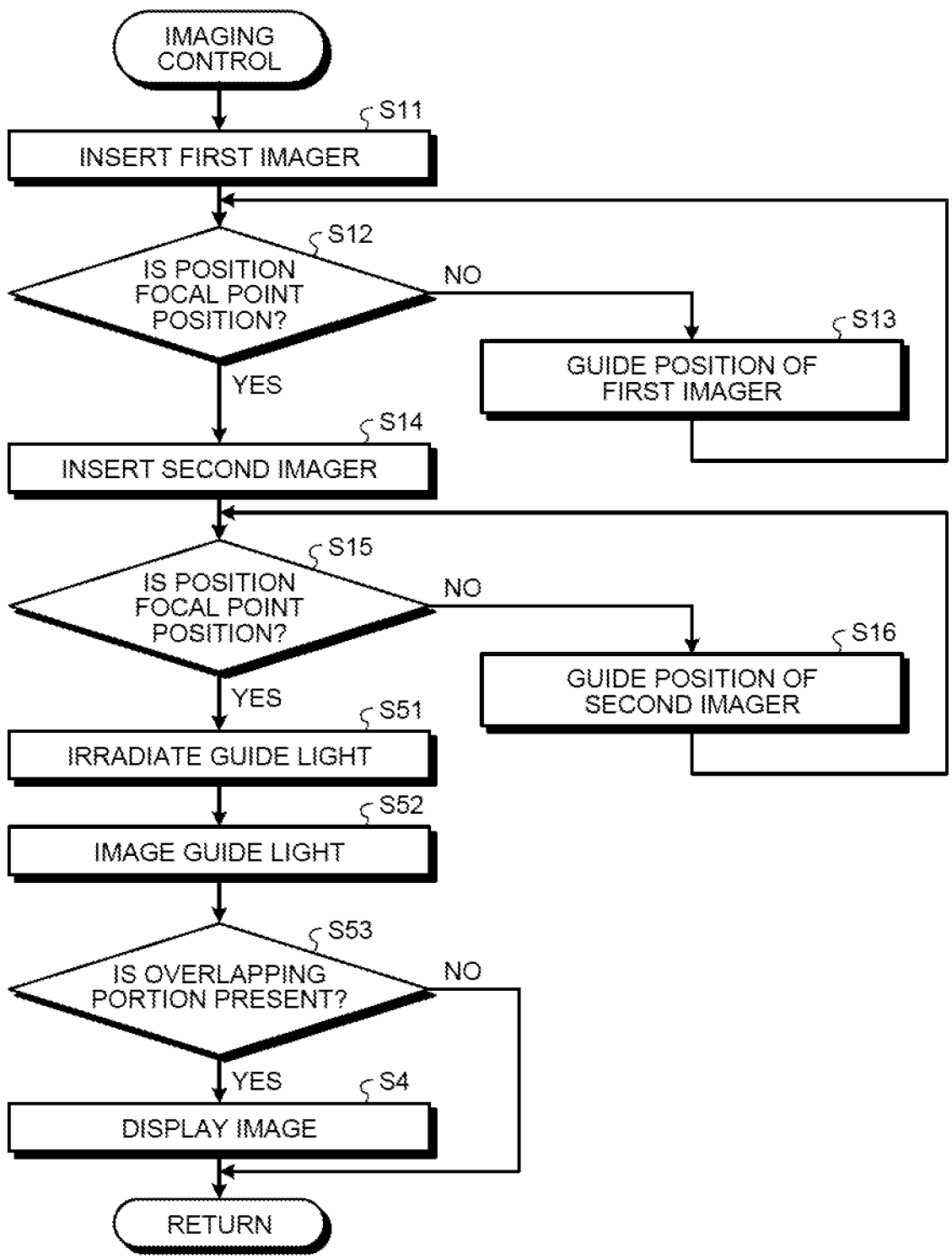
FIG. 23 is a flowchart illustrating an outline of the imaging control process illustrated in FIG. 22.
Figure 24:
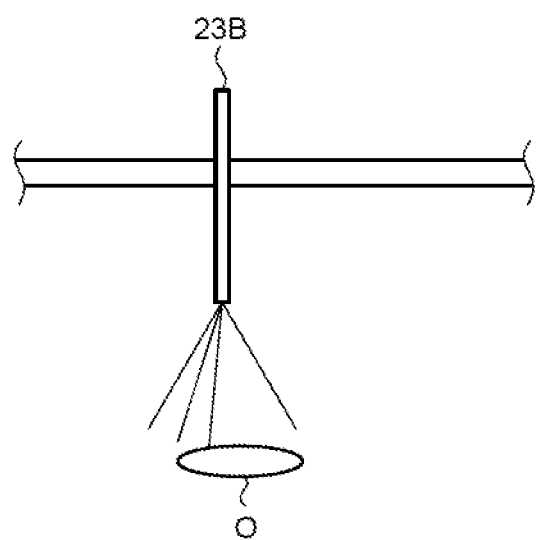
FIG. 24 is a diagram illustrating a state in which a guide light irradiator irradiates an observation target with guide light.

After that, the image processing apparatus 5 performs an imaging control process (Step S42). FIG. 23 is a flowchart illustrating an outline of the imaging control process illustrated in FIG. 22. As illustrated in FIG. 23, in the imaging control process, the same processes as those performed in the first embodiment up to Step S15, and then, the guide light irradiator 23B irradiates the observation target O with guide light (Step S51). FIG. 24 is a diagram illustrating a state in which the guide light irradiator irradiates the observation target with guide light. As illustrated in FIG. 24, guide light is irradiated from the guide light irradiator 23B onto the observation target O.

Figure 25:
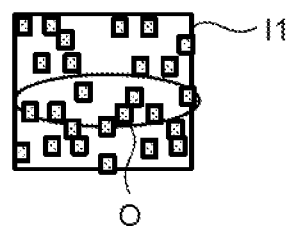
FIG. 25 is a diagram illustrating an example of guide light captured by the first imager.

Subsequently, the first imager 3 and the second imager 4 that images the guide light irradiated from the guide light irradiator 23B onto the observation target O (Step S52). FIG. 25 is a diagram illustrating an example of the guide light imaged by the first imager. As illustrated in FIG. 25, a random pattern of the guide light is included in a first image I1 that is captured by the first imager 3.

Then, the determination unit 53 determines whether or not an overlapping portion is present in the imaging areas included in the first image and the second image that are captured by the first imager 3 and the second imager 4, respectively (Step S53: a determination step). Specifically, the determination unit 53 determines whether or not an overlapping portion by comparing the pattern of the guide light included in the first image to the pattern of the guide light included in the second image.

If the determination unit 53 determines that an overlapping portion is present in the imaging areas of the first image and the second image (Yes at Step S53), the image composition unit 54 composes the first image and the second image (Step S54: an image composition step). Specifically, the image composition unit 54 compares the guide light on the first image and the second image that are captured by the first imager 3 and the second imager 4, respectively, and generates a composite image that is composed of the first image and the second image. Furthermore, it is preferable that the image composition unit 54 aligns the position of the first image with the position of the second image by using the guide light and stops irradiation of the guide light, and then, composes the first image and the second image that are captured. It is possible to more accurately perform position adjustment using the guide light, and an observation of the observation target O is not obstructed by the guide light.

According to the third embodiment described above, it is possible to more accurately compose images by determining whether or not an overlapping portion is present by using the guide light irradiated by the guide light irradiator 23B and composing the first image and the second image.

Furthermore, in the third embodiment, the diameter of the insertion portion 123B included in the guide light irradiator 23B is equal to or less than 3 mm, so that it is possible to perform an endoscopic operation such that an incision is not left on the subject H.

Fourth Embodiment

Figure 26:
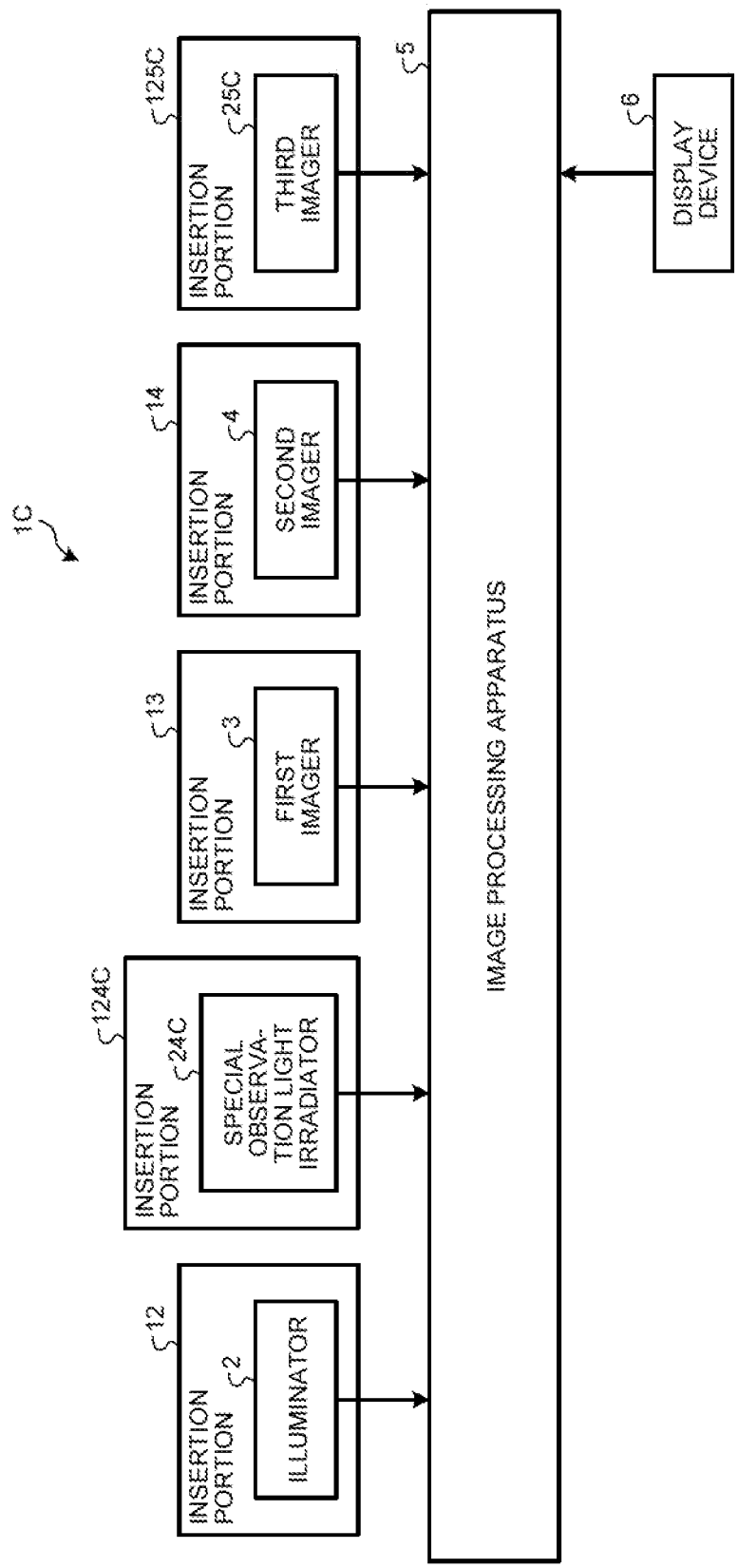
FIG. 26 is a block diagram illustrating a configuration of an observation system according to a fourth embodiment.

FIG. 26 is a block diagram illustrating a configuration of an observation system according to a fourth embodiment. As illustrated in FIG. 26, an observation system 1C includes a special observation light irradiator 24C and a third imager 25C. The other configurations may be the same as those described in the first embodiment; therefore, descriptions thereof will be omitted.

The special observation light irradiator 24C irradiates the observation target O with special observation light. The special observation light irradiator 24C is attached to the subject H by being inserted in an insertion portion 124C that is punctured into the subject H. The insertion portion 124C is a rigid needle and is not bendable with a diameter between, for example, 2 mm and 3 mm, inclusive. A light source constituted by an LED or the like and a battery that supplies electrical power to the light source are provided on the side opposite to the insertion portion 124C included in the special observation light irradiator 24C. The special observation light emitted by the light source is irradiated on the observation target O via a lens or an optical fiber that is disposed in an inside of the insertion portion 124C. However, the special observation light irradiator 24C may irradiate the observation target O with the special observation light that is output by an external light source device. The special observation light is special observation light that is used for, for example, a narrow band imaging (NBI) observation, an infrared imaging (IRI) observation, or a fluorescent observation, and is light with a spectrum that is different from that of normal illumination light.

The third imager 25C captures an image of the observation target O at a position that is different from positions at which the first imager 3 and the second imager 4 capture the images of the observation target O. The third imager 25C is attached to the subject H by being inserted into an insertion portion 125C that is a rigid needle and is not bendable with a diameter between, for example, 2 mm and 3 mm, inclusive. As a result of the insertion portion 125C being punctured into a position of the subject H that is different from positions in which the insertion portion 13 and the insertion portion 14 are inserted, an image of the observation target O is captured at a position that is different from positions at which the first imager 3 and the second imager 4 capture the images of the observation target O. An imaging element that is constituted by using an image sensor including a CCD image sensor or CMOS image sensor, an A/D conversion circuit, and the like is provided on the side opposite to the insertion portion 125C of the third imager 25C. Then, reflected light from the observation target O is imaged by the imaging element via a lens or an optical fiber that is disposed in an inside of the insertion portion 125C. The imaging element included in the third imager 25C has sensitivity in a spectrum of the special observation light irradiated by the special observation light irradiator 24C and is an imaging element that is suitable for a special light observation performed by using special observation light.

According to the fourth embodiment described above, it is possible to perform a normal endoscope observation by irradiating illumination light from the illuminator 2 and capturing images by using the first imager 3 and the second imager 4, and it is possible to perform a special light observation, such as an NBI observation, an IRI observation, or a fluorescent observation by irradiating the special observation light from the special observation light irradiator 24C and capturing images using the third imager 25C.

In addition, in the fourth embodiment, the diameter of each of the insertion portion 124C included in the special observation light irradiator 24C and the insertion portion 125C included in the third imager 25C, respectively, is equal to or less than 3 mm, so that it is possible to perform an endoscopic operation using the special observation light such that an incision is not left on the subject H.

Various embodiments may be made by appropriately combining a plurality of components disclosed in the image processing apparatus according to one embodiment of the present disclosure described above. For example, some components may be deleted from all of the components described in the image processing apparatus according to the embodiment of the present disclosure described above. Furthermore, the components described in the image processing apparatus according to the embodiment of the present disclosure described above may be appropriately combined.

Furthermore, in the image processing apparatus according to one embodiment of the present disclosure, the "unit" described above may be replaced with a "means", a "circuit", or the like. For example, the control unit may be replaced with a control means or a control circuit.

Moreover, the programs to be executed by the image processing apparatus according to one embodiment of the present disclosure are provided by being recorded, as file data in an installable format or an executable format, on a computer readable recording medium such as a compact disk read only memory (CD-ROM), a flexible disk (FD), a compact disk recordable (CD-R), a digital versatile disk (DVD), a universal serial bus (USB) medium, or a flash memory.

Furthermore, the programs to be executed by the information providing system according to one embodiment of the present disclosure may be stored on a computer connected to a network, such as the Internet, and provided by being downloaded via the network.

Furthermore, in a description of the flowcharts in the application, the relationship between before and after the processes performed at each step is stated by using "first", "then", "subsequently", and the like; however, the order of the processes needed to implement the disclosure is not uniquely determined by the descriptions above. Specifically, the order of the processes in the flowcharts described in the application may also be changed as long as processes do not conflict with each other. Furthermore, the processes need not always be implemented by simple branch processing, but may be branched based on comprehensive determination on the increased number of determination items. In this case, it may be possible to additionally use an artificial intelligence technology that realizes machine learning by repetition of learning by requesting a user to perform manual operation. In addition, it may be possible to perform learning of operation patterns that are implemented by a large number of specialists, and perform the processes by deep learning with further inclusion of complicated conditions.

According to the disclosure, it is possible to implement an image processing apparatus, observation system, and an observation method capable of sufficiently ensure a field of view in an endoscopic operation.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An observation system comprising a processor comprising hardware, the processor being configured to:
   determine whether or not an overlapping portion is present in imaging areas included in a plurality of images captured by a plurality of imagers, respectively, the plurality of imagers being are inserted into a subject to capture images of an observation target at different positions from each other;
   determine whether or not each of the plurality of imagers is inserted to a focal point position at which the observation target is in focus;
   generate a composite image that is composed of the plurality of images when it is determined that each of the plurality of imagers is inserted to the focal point position and that the overlapping portion is present in the imaging areas;
   perform at least one of a voice output, outputting characters to a display, and projecting a marker that indicates a puncture position at which each of the plurality of imagers is to be punctured into the subject to guide the puncture position on the subject, and
   perform at least one of a voice output and outputting characters to a display to guide a positional relationship between each of the plurality of images and the observation target to insert each of the plurality of imagers to the focal point position,
   wherein the plurality of imagers are configured to capture the plurality of images.

2. The observation system according to claim 1, wherein the observation target is irradiated with illumination light emitted from a plurality of illuminators configured to irradiate the illumination light from different positions from each other, wherein
   the processor is further configured to:
   determine whether or not a luminance distribution of the composite image is uniform;
   guide, based on a determination result of the luminance distribution of the composite image, a position of each of the plurality of illuminators and an intensity of light irradiated onto the observation target by each of the plurality of illuminators; and
   control a distance between each of the plurality of illuminators and the observation target to make the luminance distribution of the composite image uniform.

3. The observation system according to claim 1, wherein the plurality of imagers are attached to the subject by being inserted in respective insertion portions that are punctured into the subject at different positions from each other.

4. The observation system according to claim 3, wherein a diameter of each of the insertion portions is equal to or less than 3 mm.

5. The observation system according to claim 1, further comprising a position detector configured to acquire positional information on each of the plurality of imagers, wherein
the processor is further configured to determine, based on the positional information, whether or not the overlapping portion is present in the imaging areas included in the plurality of images.

6. The observation system according to claim 1, further comprising an illuminator configured to irradiate the observation target with illumination light.

7. The observation system according to claim 6, wherein the illuminator is attached to the subject by being inserted in an insertion portion that is punctured into the subject, and
a diameter of the insertion portion is equal to or less than 3 mm.

8. The observation system according to claim 6, wherein the illuminator includes a plurality of illuminators configured to irradiate the observation target with illumination light from different positions from each other.

9. The observation system according to claim 8, wherein the plurality of illuminators are attached to the subject by being inserted in respective insertion portions that are punctured into the subject at different positions from each other.

10. The observation system according to claim 9, wherein a diameter of each of the insertion portions is equal to or less than 3 mm.

11. The observation system according to claim 6, wherein the illuminator includes a guide light irradiator configured to irradiate the observation target with guide light, and
the processor is further configured to
   determine whether or not the overlapping portion is present in the imaging areas included in the plurality of images by comparing the guide light on the plurality of images captured by the plurality of respective imagers, and
   generate the composite image by comparing the guide light on the plurality of images captured by the plurality of respective imagers.

12. The observation system according to claim 11, wherein
the guide light irradiator is attached to the subject by being inserted in an insertion portion that is punctured into the subject, and
a diameter of the insertion portion is equal to or less than 3 mm.

13. The observation system according to claim 6, wherein the illuminator includes a special observation light irradiator configured to irradiate the observation target with special observation light.

14. The observation system according to claim 13, wherein
the special observation light irradiator is attached to the subject by being inserted in an insertion portion that is punctured into the subject, and
a diameter of the insertion portion is equal to or less than 3 mm.

15. An observation method comprising:
ensuring an observation purpose space for observing an observation target located inside a subject;
inserting, into the subject, a plurality of imagers configured to capture images of the observation target at different positions from each other;
guiding the plurality of imagers to a focal point position at which the observation target is in focus;
determining whether or not an overlapping portion is present in imaging areas included in a plurality of images captured by the plurality of imagers, respectively;

generating, when it is determined that the overlapping portion is present at the determining, a composite image that is composed of the plurality of images;

performing at least one of a voice output, outputting characters to a display, and projecting a marker that indicates a puncture position at which each of the plurality of imagers is to be punctured into the subject to guide the puncture position on the subject, and performing at least one of a voice output and outputting characters to a display to guide a positional relationship between each of the plurality of images and the observation target to insert each of the plurality of imagers to the focal point position, wherein the plurality of imagers are configured to capture the plurality of images.

16. An observation system comprising a processor comprising hardware, the processor being configured to:

determine whether or not an overlapping portion is present in imaging areas included in a plurality of images captured by a plurality of imagers, respectively, the plurality of imagers being configured to capture images of an observation target at different positions from each other, the observation target being located inside a subject and that is irradiated with illumination light;

generate, when it is determined that the overlapping portion is present in the imaging areas, a composite image that is composed of the plurality of images in which unevenness of brightness of the overlapping portion is reduced;

perform at least one of a voice output, outputting characters to a display, and projecting a marker that indicates a puncture position at which each of the plurality of imagers is to be punctured into the subject to guide the puncture position on the subject, and perform at least one of a voice output and outputting characters to a display to guide a positional relationship between each of the plurality of images and the observation target to insert each of the plurality of imagers to a focal point position, wherein the plurality of imagers are configured to capture the plurality of images.

17. An observation system comprising:

a processor comprising hardware, the processor being configured to determine whether or not an overlapping portion is present in imaging areas included in a plurality of images captured by a plurality of imagers, respectively, the plurality of imagers being are inserted into a subject to capture images of an observation target at different positions from each other, and generate a composite image that is composed of the plurality of images when it is determined that the overlapping portion is present in the imaging areas; and an illuminator that includes a guide light irradiator configured to irradiate the observation target with guide light, wherein the processor is configured to determine whether or not the overlapping portion is present in the imaging areas by comparing the guide light on the plurality of images captured by the plurality of respective imagers, generate the composite image by comparing the guide light on the plurality of images captured by the plurality of respective imagers;

perform at least one of a voice output, outputting characters to a display, and projecting a marker that indicates a puncture position at which each of the plurality of imagers is to be punctured into the subject to guide the puncture position on the subject, and perform at least one of a voice output and outputting characters to a display to guide a positional relationship between each of the plurality of images and the observation target to insert each of the plurality of imagers to a focal point position, wherein the plurality of imagers are configured to capture the plurality of images.

* * * * *